(12) United States Patent
Hebert et al.

(10) Patent No.: US 8,876,876 B2
(45) Date of Patent: *Nov. 4, 2014

(54) PROSTHESIS AND DELIVERY SYSTEM

(75) Inventors: Stephen Hebert, San Francisco, CA (US); Marc-Alan Levine, Pottstown, PA (US)

(73) Assignee: Back Bay Medical Inc., Costa Mesa, CA (US)

( * ) Notice: Subject to any disclaimer, the term of this patent is extended or adjusted under 35 U.S.C. 154(b) by 1120 days.

This patent is subject to a terminal disclaimer.

(21) Appl. No.: 12/134,591

(22) Filed: Jun. 6, 2008

(65) Prior Publication Data
US 2009/0306761 A1 Dec. 10, 2009

(51) Int. Cl.
| | |
|---|---|
| *A61F 2/06* | (2013.01) |
| *A61F 2/91* | (2013.01) |
| *A61F 2/915* | (2013.01) |
| *A61F 2/966* | (2013.01) |
| *A61F 2/00* | (2006.01) |
| *A61F 2/95* | (2013.01) |

(52) U.S. Cl.
CPC ........... *A61F 2/95* (2013.01); *A61F 2250/0098* (2013.01); *A61F 2002/91583* (2013.01); *A61F 2/915* (2013.01); *A61F 2002/9665* (2013.01); *A61F 2002/91558* (2013.01); *A61F 2/0095* (2013.01); *A61F 2/91* (2013.01); *A61F 2002/9505* (2013.01)
USPC ...................................................... 623/1.11

(58) Field of Classification Search
CPC ........... A61F 2/95; A61F 2/954; A61F 2/962; A61F 2/966
USPC ................ 606/108; 623/1.11–1.12, 1.15, 1.2, 623/1.23, 903
See application file for complete search history.

(56) References Cited

U.S. PATENT DOCUMENTS

| | | |
|---|---|---|
| 3,485,234 A | 12/1969 | Stevens |
| 4,586,923 A | 5/1986 | Gould et al. |
| 4,665,918 A | 5/1987 | Garza et al. |
| 4,768,507 A | 9/1988 | Fischell et al. |
| 4,990,151 A | 2/1991 | Wallstén |

(Continued)

FOREIGN PATENT DOCUMENTS

| | | |
|---|---|---|
| EP | 0686379 B2 | 12/1995 |
| EP | 0696447 B1 | 2/1996 |

(Continued)

OTHER PUBLICATIONS

"Proximal", www.merriam-webster.com/dictionary/proximal, Dec. 13, 2013, p. 1.*

(Continued)

*Primary Examiner* — Ashley Fishback
(74) *Attorney, Agent, or Firm* — Tim L. Kitchen; Peter B. Scull; Hamilton, DeSanctis & Cha, LLP

(57) ABSTRACT

A prosthesis delivery system including a prosthesis mounted on an elongate member. The prosthesis has a locking member positioned on the prosthesis. The locking member includes a reduced diameter portion with two opposing surfaces that are configured to engage opposing proximal and distal sides of a radially extending member on the elongate member to lock or limit the longitudinal position of the prosthesis on the elongate member during delivery of the prosthesis to a treatment site.

4 Claims, 39 Drawing Sheets

(56) References Cited

U.S. PATENT DOCUMENTS

| | | | |
|---|---|---|---|
| 5,368,592 A | 11/1994 | Stern et al. |
| 5,571,086 A | 11/1996 | Kaplan et al. |
| 5,683,451 A | 11/1997 | Lenker et al. |
| 5,702,418 A | 12/1997 | Ravenscroft |
| 5,755,708 A | 5/1998 | Segal |
| 5,776,141 A | 7/1998 | Klein et al. |
| 5,782,855 A | 7/1998 | Lau et al. |
| 5,788,707 A | 8/1998 | Del Toro et al. |
| 5,797,952 A | 8/1998 | Klein |
| 5,824,041 A | 10/1998 | Lenker et al. |
| 5,957,929 A | 9/1999 | Brenneman |
| 5,989,280 A | 11/1999 | Euteneuer |
| 6,024,763 A | 2/2000 | Lenker et al. |
| 6,126,685 A | 10/2000 | Lenker et al. |
| 6,171,328 B1 | 1/2001 | Addis |
| 6,179,859 B1 | 1/2001 | Bates et al. |
| 6,183,481 B1 | 2/2001 | Lee et al. |
| 6,187,015 B1 | 2/2001 | Brenneman |
| 6,214,036 B1 | 4/2001 | Letendre et al. |
| 6,245,045 B1 | 6/2001 | Stratienko |
| 6,264,671 B1 | 7/2001 | Stack et al. |
| 6,270,521 B1 | 8/2001 | Fischell et al. |
| 6,280,465 B1 | 8/2001 | Cryer |
| 6,296,622 B1 | 10/2001 | Kurz et al. |
| 6,350,278 B1 | 2/2002 | Lenker et al. |
| 6,355,060 B1 | 3/2002 | Lenker et al. |
| 6,562,064 B1 | 5/2003 | deBeer |
| 6,673,106 B2 | 1/2004 | Mitelberg et al. |
| 6,679,909 B2 | 1/2004 | McIntosh et al. |
| 6,716,238 B2 | 4/2004 | Elliott |
| 6,818,013 B2 | 11/2004 | Mitelberg et al. |
| 6,833,003 B2 | 12/2004 | Jones et al. |
| 6,840,950 B2 | 1/2005 | Stanford et al. |
| 6,939,368 B2 | 9/2005 | Simso |
| 6,955,685 B2 | 10/2005 | Escamilla et al. |
| 6,960,227 B2 | 11/2005 | Jones et al. |
| 6,989,024 B2 | 1/2006 | Hebert et al. |
| 7,001,422 B2 | 2/2006 | Escamilla et al. |
| 7,063,719 B2 | 6/2006 | Jansen et al. |
| 7,182,779 B2 | 2/2007 | Acosta et al. |
| 7,195,648 B2 | 3/2007 | Jones et al. |
| 7,201,769 B2 | 4/2007 | Jones et al. |
| 7,500,988 B1 * | 3/2009 | Butaric et al. ............... 623/1.16 |
| 2001/0027323 A1 | 10/2001 | Sullivan, III et al. |
| 2001/0037126 A1 | 11/2001 | Stack et al. |
| 2002/0120323 A1 | 8/2002 | Thompson et al. |
| 2004/0010265 A1 | 1/2004 | Karpiel |
| 2004/0193178 A1 | 9/2004 | Nikolchev |
| 2004/0193179 A1 | 9/2004 | Nikolchev |
| 2004/0220585 A1 | 11/2004 | Nikolchev |
| 2005/0038496 A1 | 2/2005 | Jones et al. |
| 2005/0049666 A1 | 3/2005 | Chien et al. |
| 2005/0049668 A1 | 3/2005 | Jones et al. |
| 2005/0049670 A1 | 3/2005 | Jones et al. |
| 2005/0209670 A1 | 9/2005 | George et al. |
| 2005/0209671 A1 | 9/2005 | Ton et al. |
| 2005/0209672 A1 | 9/2005 | George et al. |
| 2005/0209675 A1 | 9/2005 | Ton et al. |
| 2006/0041302 A1 | 2/2006 | Malewicz |
| 2006/0085057 A1 | 4/2006 | George et al. |
| 2006/0111771 A1 * | 5/2006 | Ton et al. ............... 623/1.15 |
| 2006/0149355 A1 | 7/2006 | Mitelberg et al. |
| 2006/0200221 A1 | 9/2006 | Malewicz |
| 2006/0204547 A1 | 9/2006 | Nguyen et al. |
| 2006/0206200 A1 | 9/2006 | Garcia et al. |
| 2006/0206201 A1 | 9/2006 | Garcia et al. |
| 2006/0271149 A1 | 11/2006 | Berez et al. |
| 2006/0271153 A1 | 11/2006 | Garcia et al. |
| 2007/0027522 A1 | 2/2007 | Chang et al. |
| 2007/0043419 A1 | 2/2007 | Nikolchev et al. |
| 2007/0043420 A1 | 2/2007 | Lostetter |
| 2007/0055339 A1 | 3/2007 | George et al. |
| 2007/0073379 A1 | 3/2007 | Chang |
| 2007/0083256 A1 | 4/2007 | Dorn |
| 2007/0156223 A1 | 7/2007 | Vaughan |
| 2007/0208407 A1 | 9/2007 | Gerdts et al. |
| 2007/0219617 A1 | 9/2007 | Saint |
| 2007/0255385 A1 | 11/2007 | Tenne et al. |
| 2007/0255386 A1 | 11/2007 | Tenne |
| 2008/0114442 A1 | 5/2008 | Mitchell et al. |

FOREIGN PATENT DOCUMENTS

| | | |
|---|---|---|
| EP | 0792627 B2 | 9/1997 |
| EP | 0943302 B1 | 9/1999 |
| EP | 1157673 A2 | 11/2001 |
| WO | WO0012030 A1 | 3/2000 |
| WO | WO02067782 A2 | 9/2002 |
| WO | WO02067782 A3 | 9/2002 |

OTHER PUBLICATIONS

Cordis Neurovascular, Inc., Rapidtransit Microcatheter 18 System through tortuous vasculature, 2002, Miami Lakes, FL.

Randall T. Higashida, et al., Initial Clinical Experience with a New Self-Expanding Nitinol Stent for the Treatment of Intracranial Cerebral Aneurysms: The Gordis Enterprose Stent, AJNR Am J Neuroradiol, Aug. 2005, 26:1751-1756, American Society of Neuroradiology.

Alexandre C. Abizaid, et al., The CardioMind Coronary Stent Delivery System: Stent Delivery on a .014" Guidewire Platform, EuroIntervention, Europa Edition 2007, 3:154-157, EuroPCROnline (Europa Edition).

Notification of Transmittal of the International Search Report and the Written Opinion of the International Searching Authority, or the Declaration for International Application No. PCT/US2009/046633.

* cited by examiner

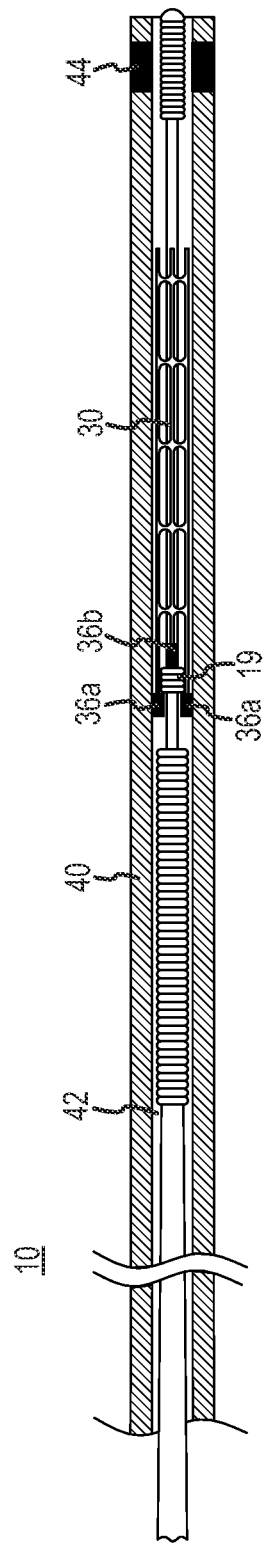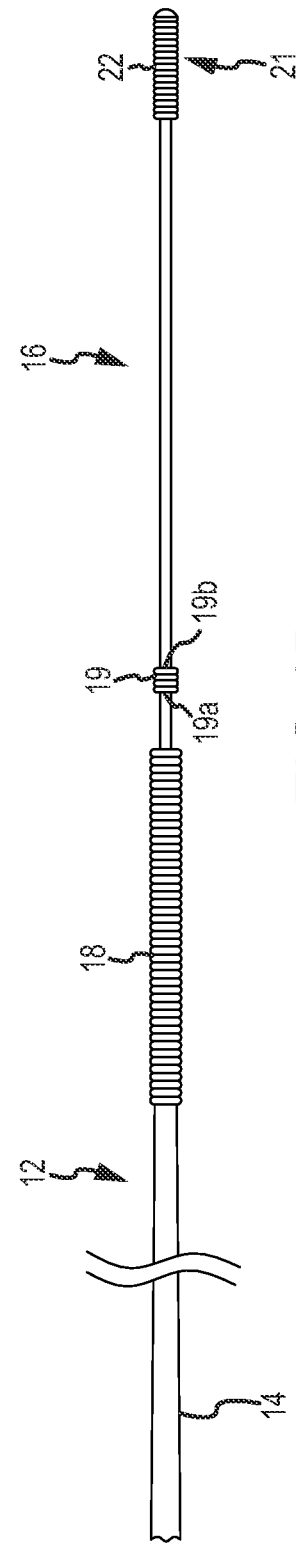

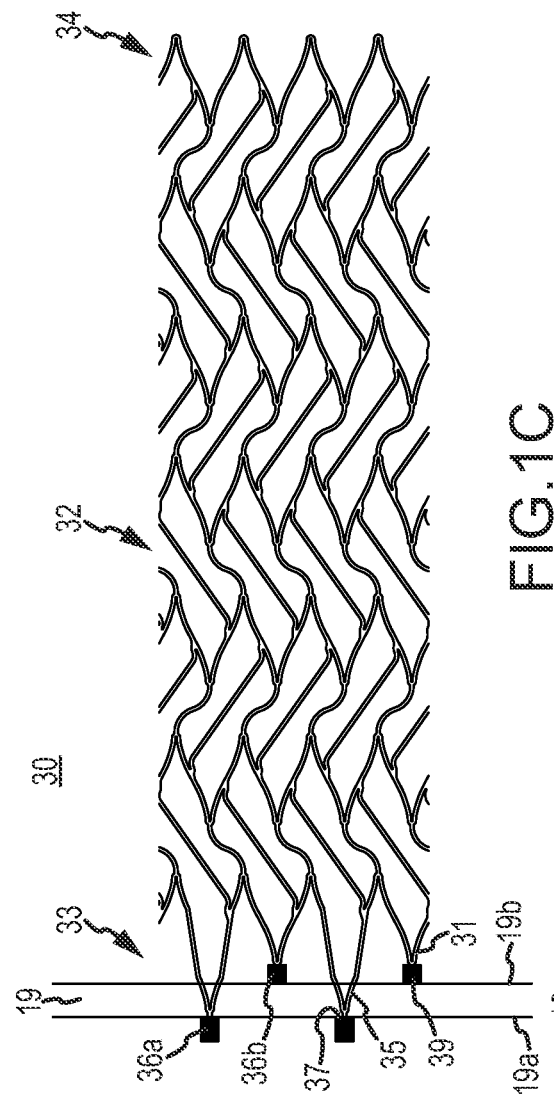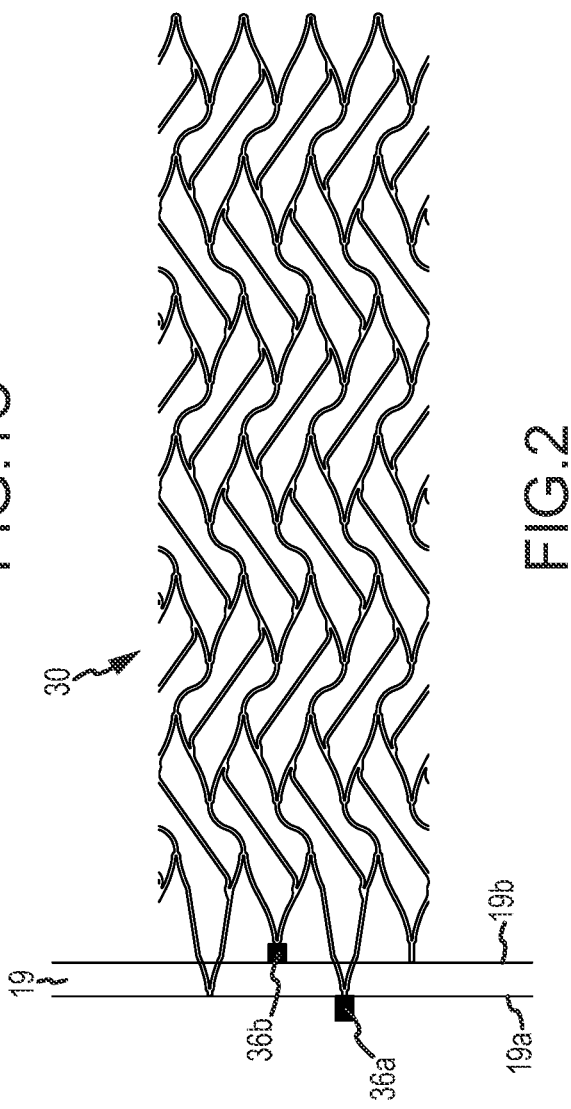

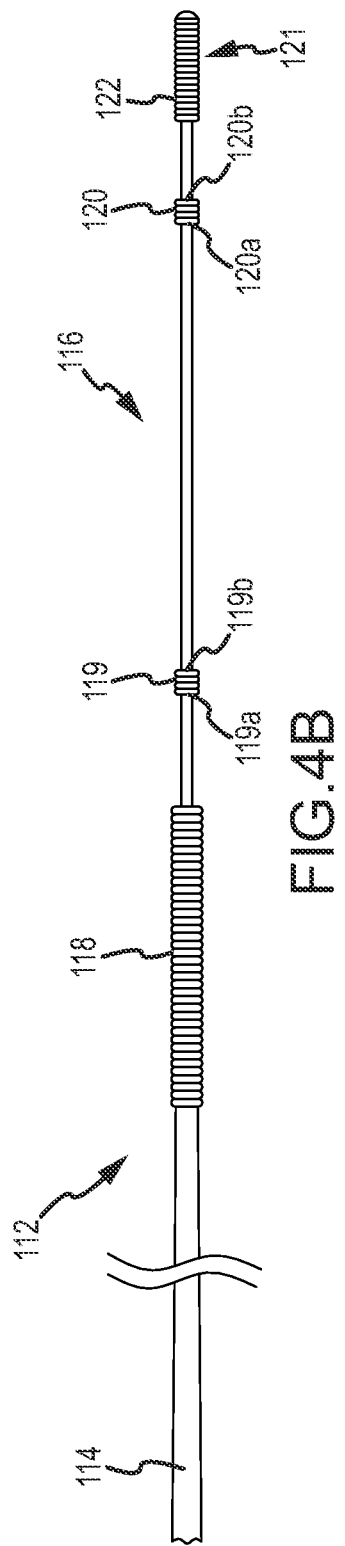
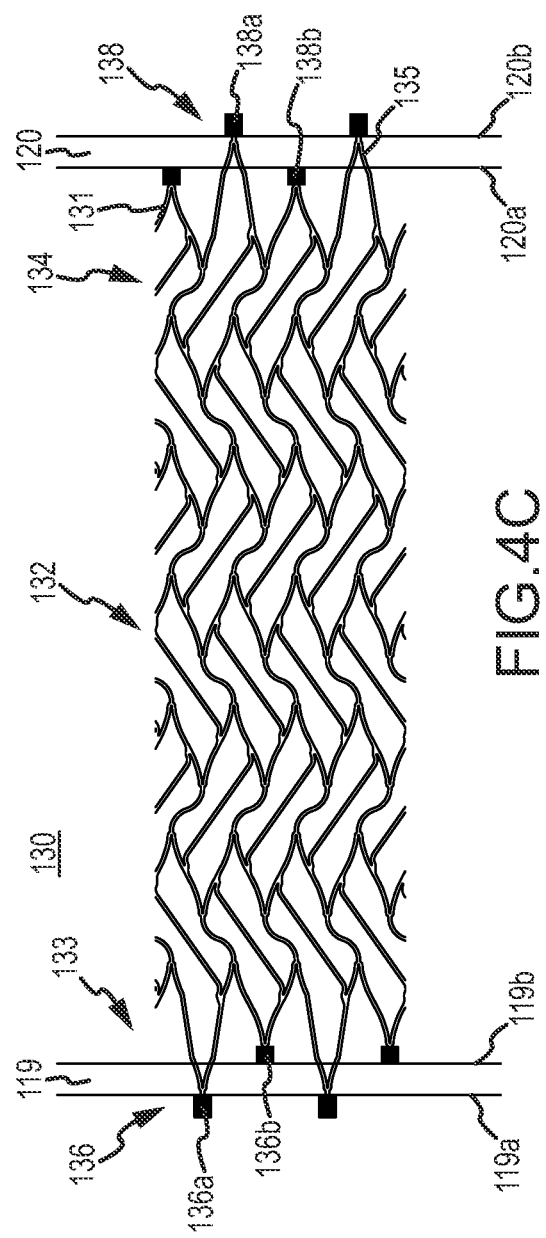

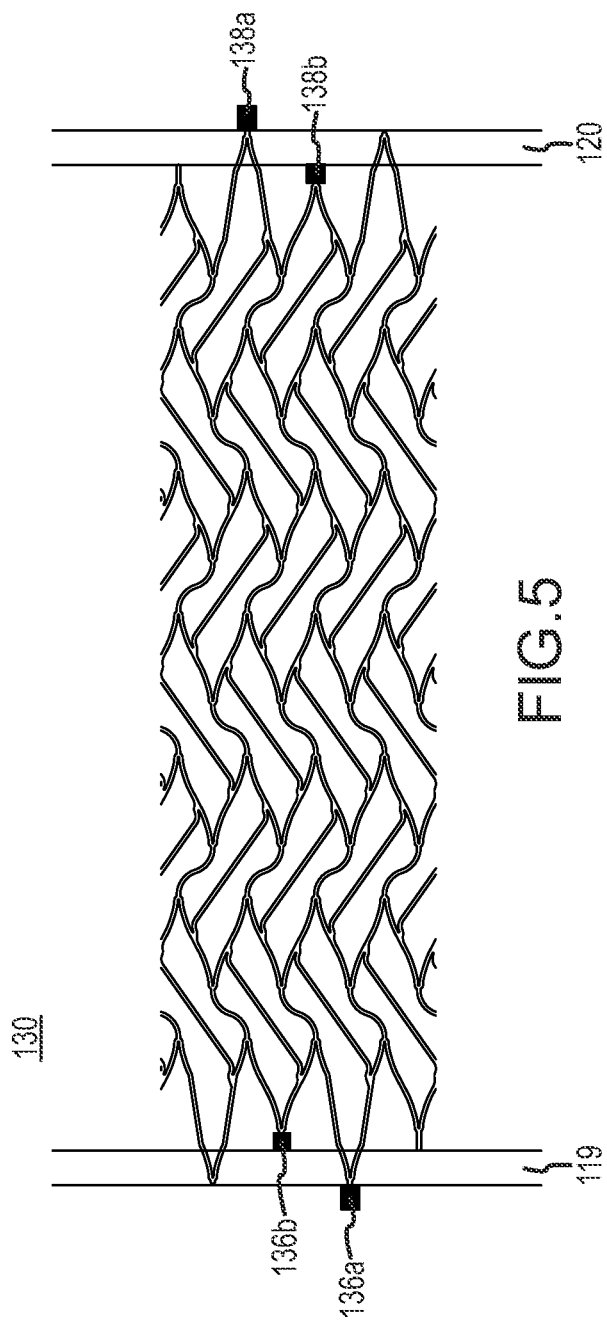

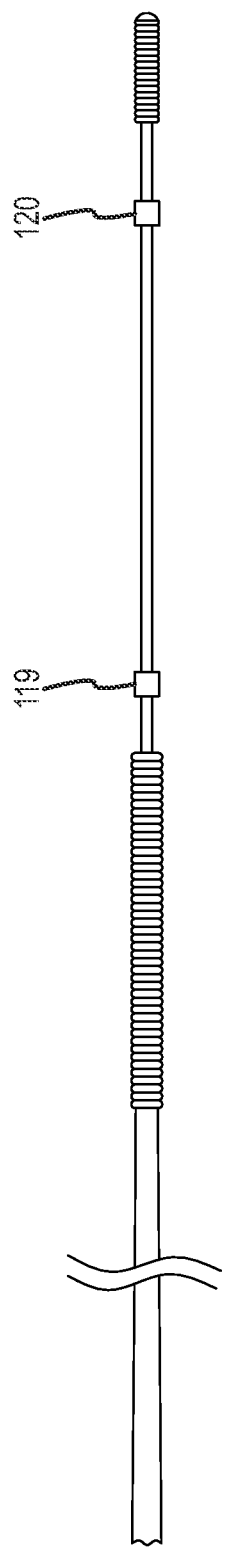

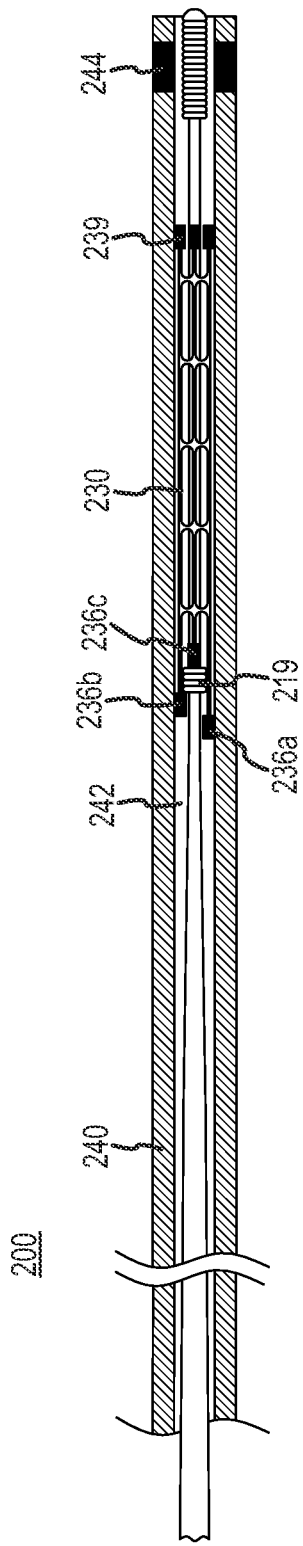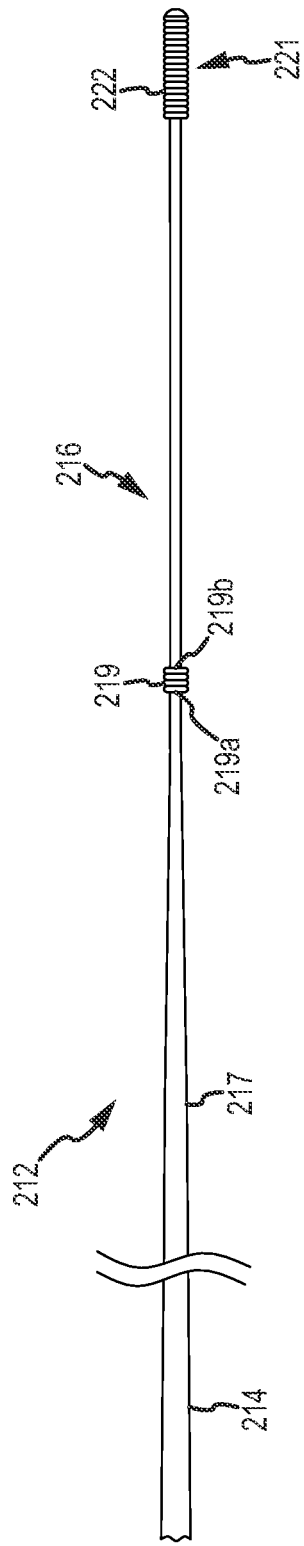
FIG.15A
FIG.15B

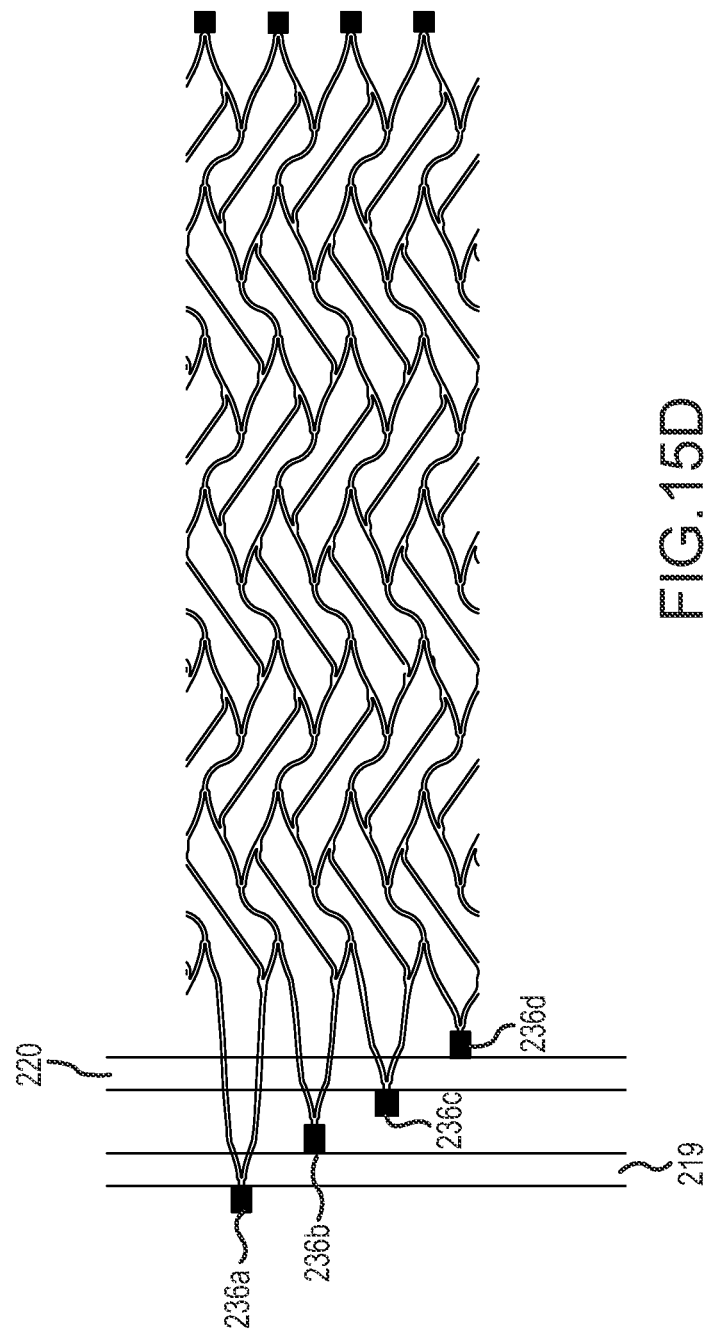

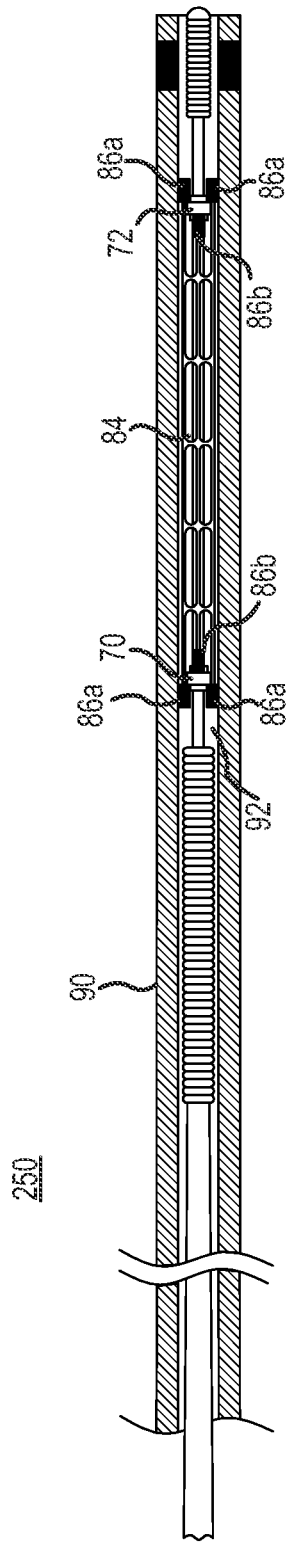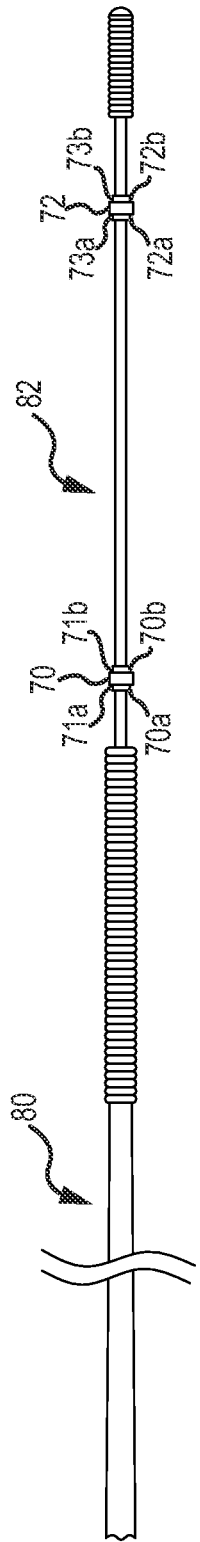
FIG.16A
FIG.16B

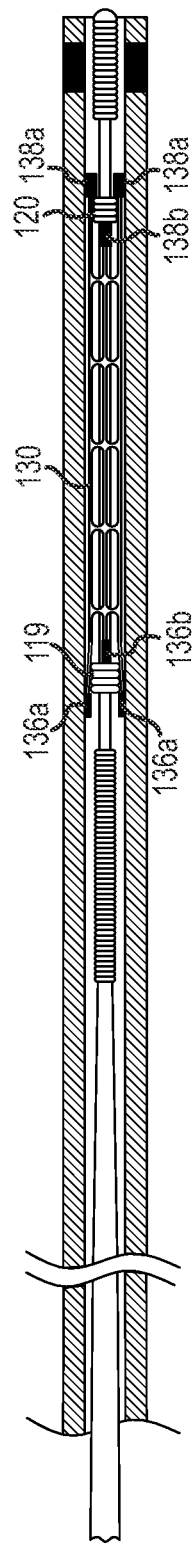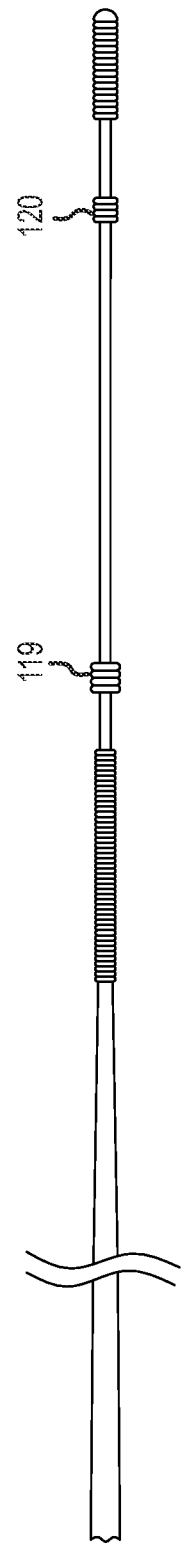
FIG. 17A
FIG. 17B

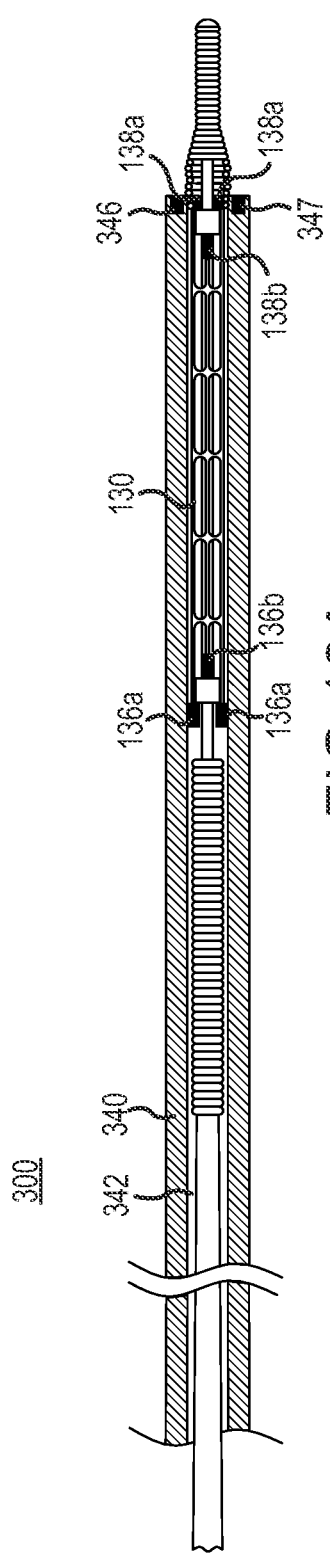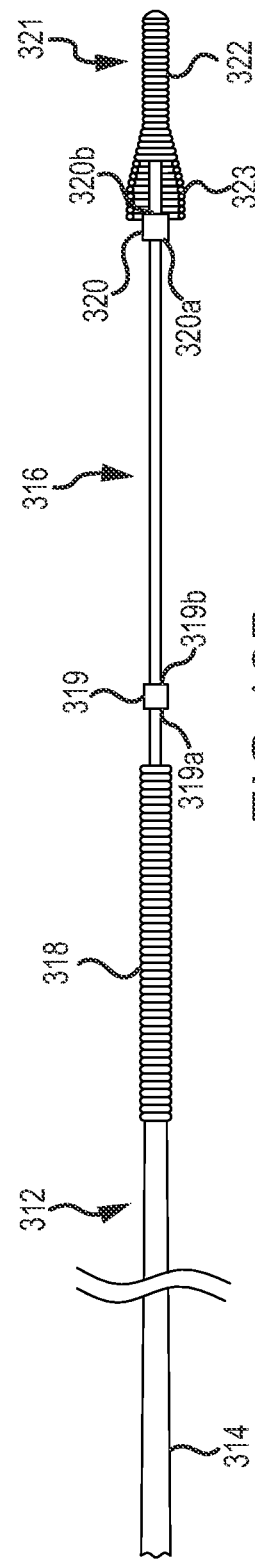
FIG. 18A
FIG. 18B

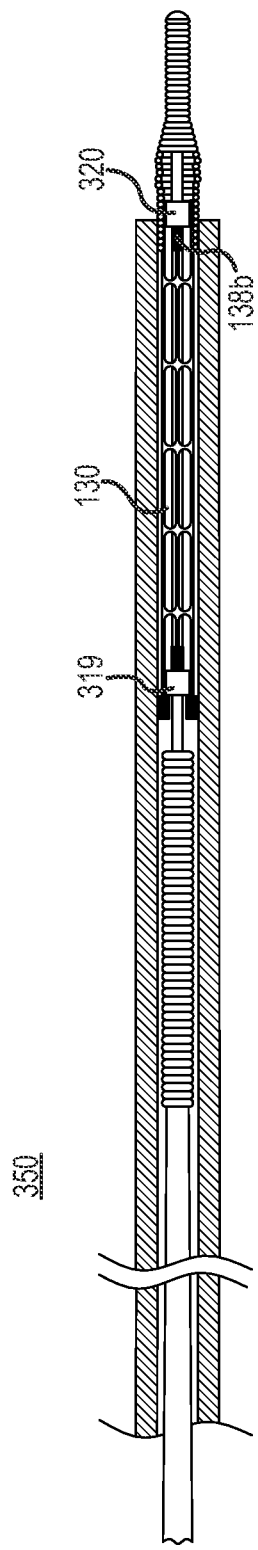
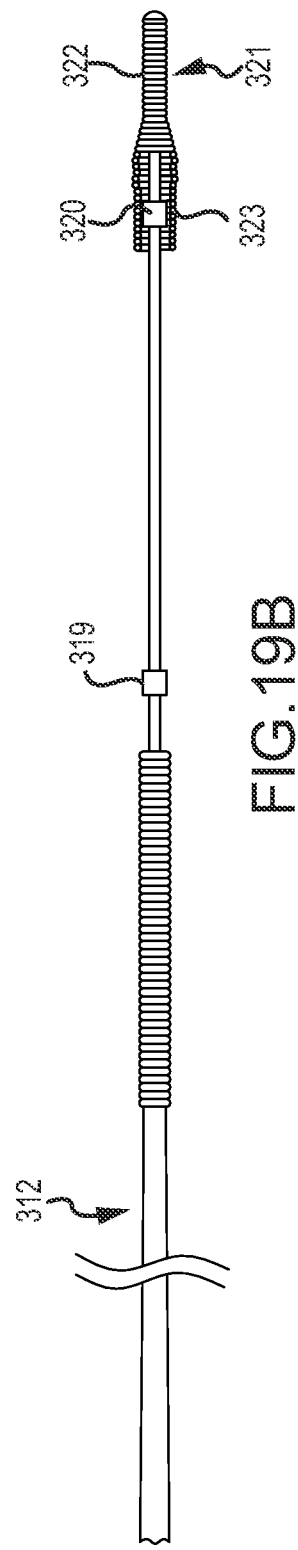

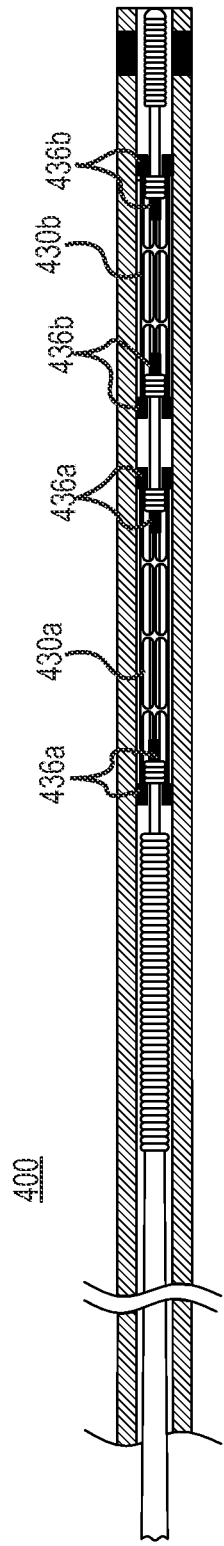
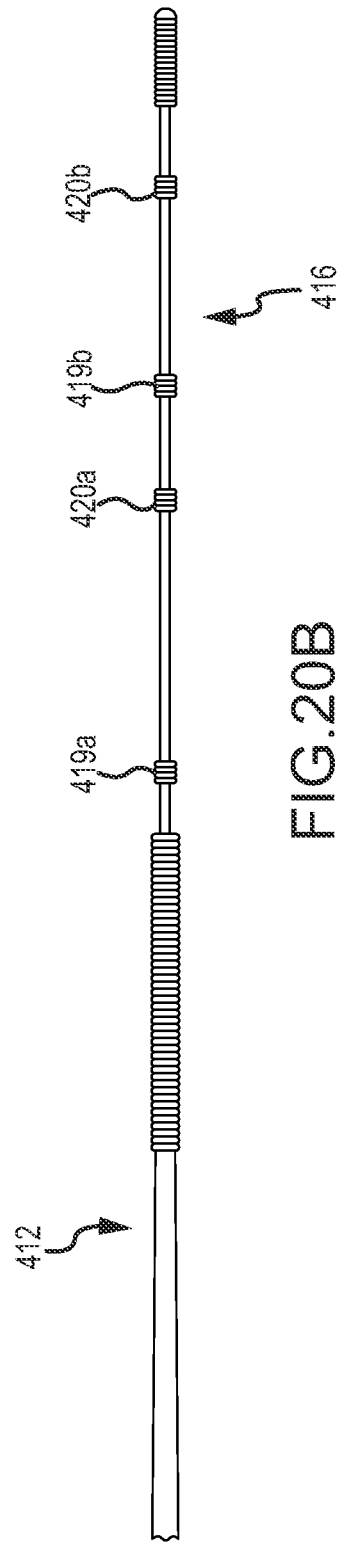
FIG.20A
FIG.20B

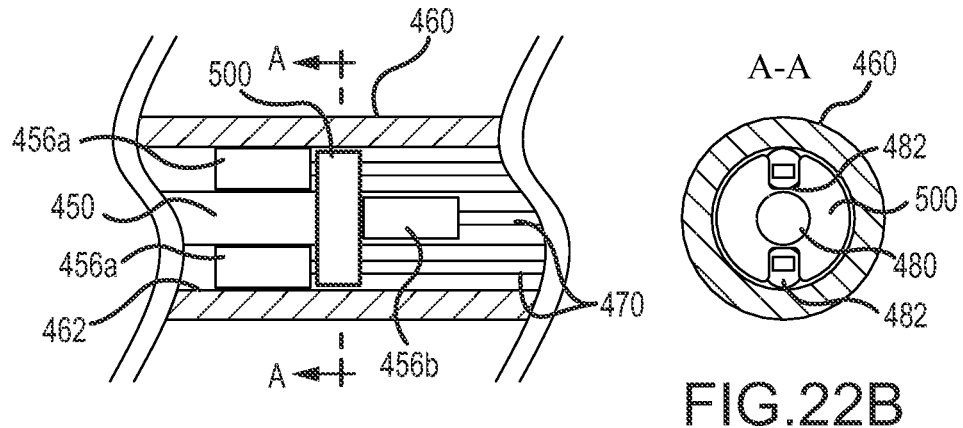
FIG.22A
FIG.22B
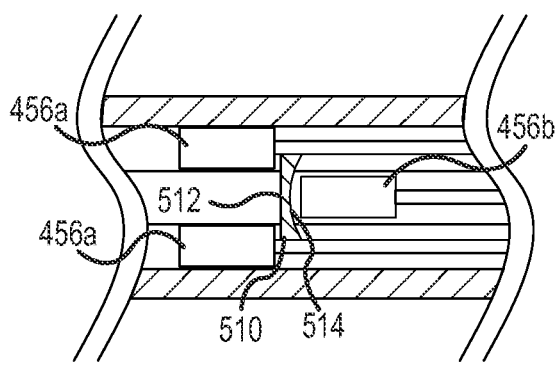
FIG.23
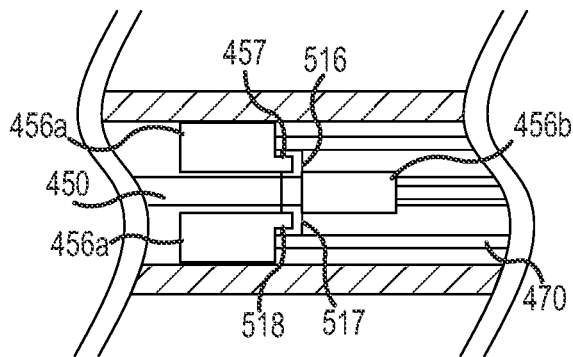
FIG.24

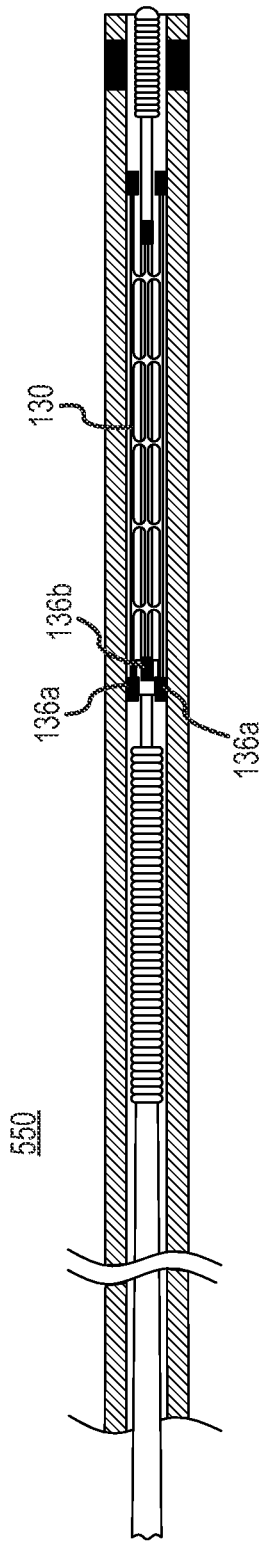
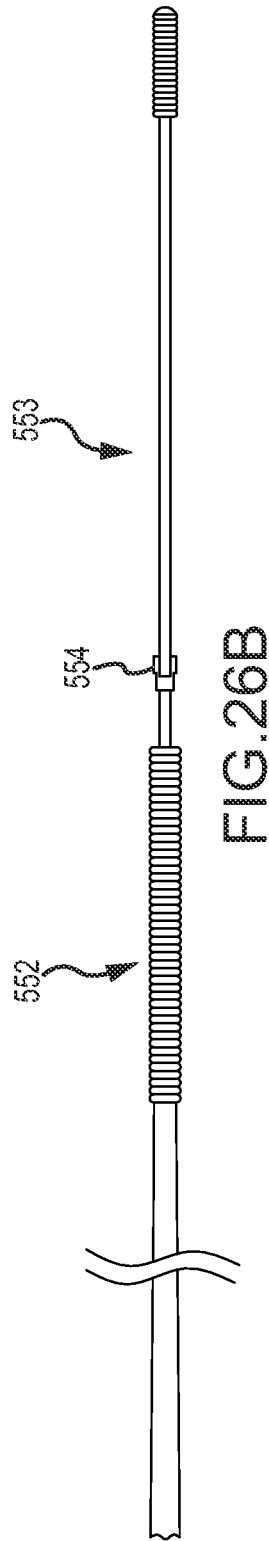
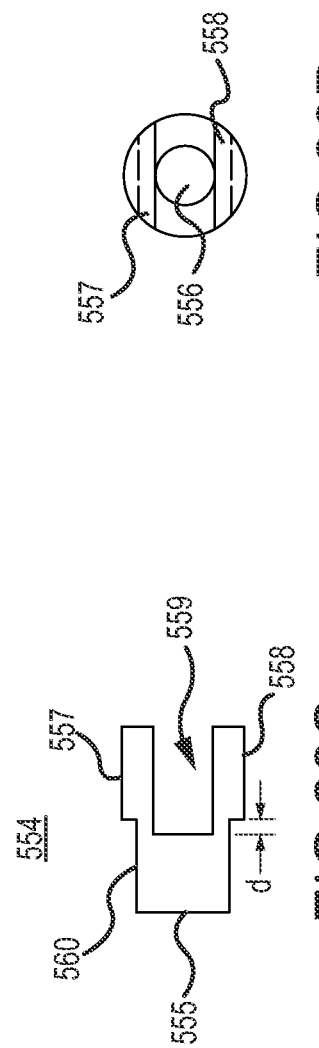
FIG.26A
FIG.26B
FIG.26D
FIG.26C

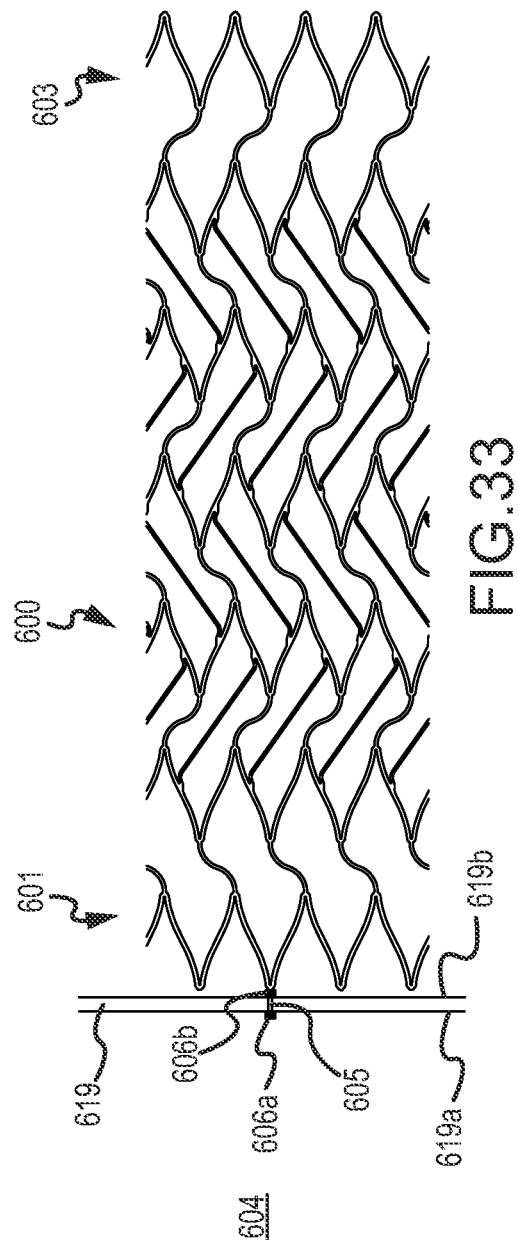
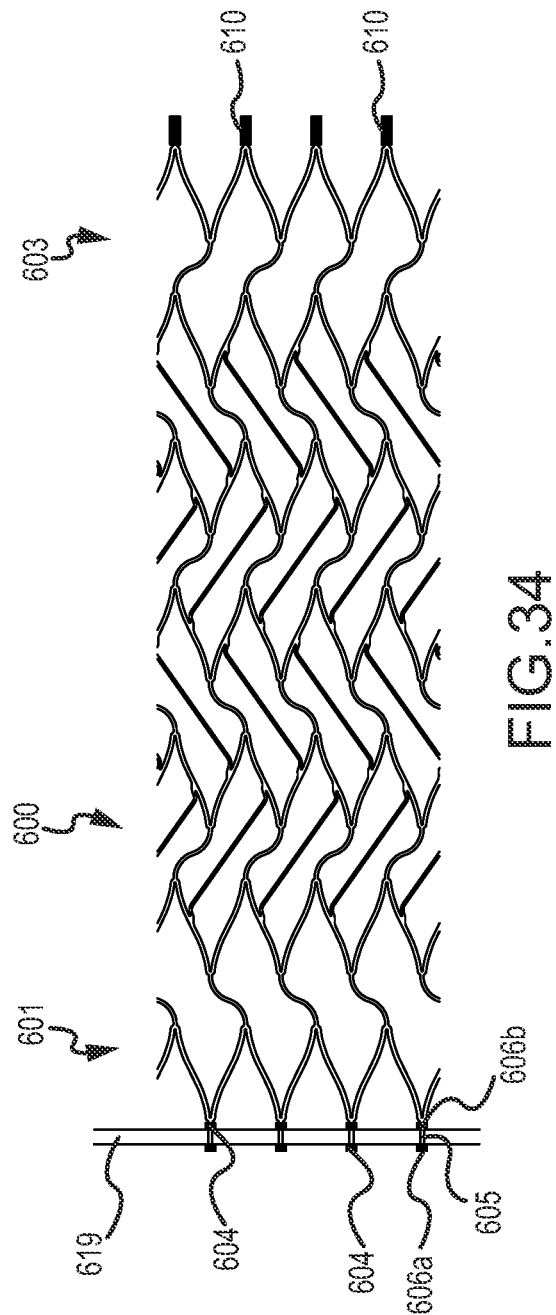
FIG.33
FIG.34

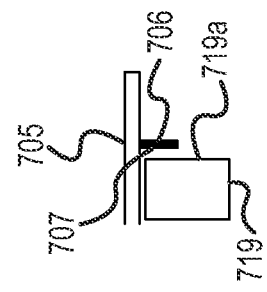
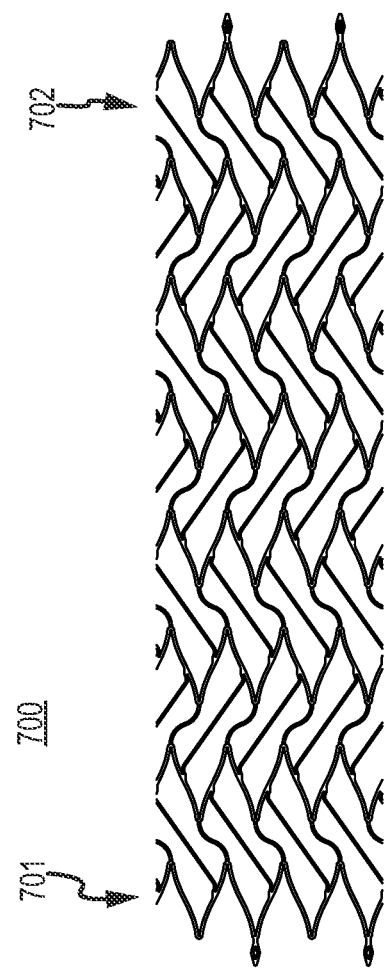
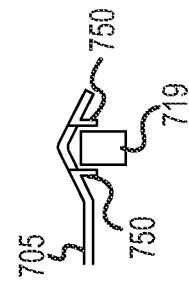
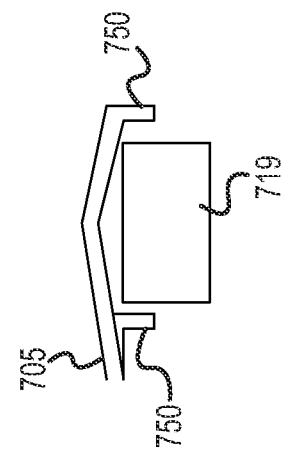
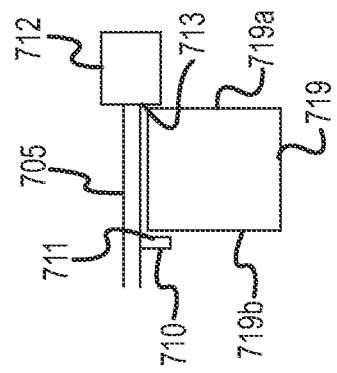

PROSTHESIS AND DELIVERY SYSTEM

TECHNICAL FIELD

This application relates to devices for implantation at a treatment site within a duct of a patient and delivery systems for carrying the devices to the treatment site.

BACKGROUND

Self-expanding prostheses, such as stents, covered stents, vascular grafts, flow diverters, and the like have been developed to treat ducts within the animal body. Many of the prostheses have been developed to treat blockages within the vasculature and aneurysms that occur in the brain. Delivery of a self-expanding prosthesis to a treatment site has traditionally involved securing the prosthesis to an outer distal segment of an elongate polymeric delivery catheter by use of a removable sheath and then advancing the delivery catheter through the vasculature to the treatment site. When properly positioned, removal of the sheath permits the prosthesis to self-expand into contact with the vessel wall being treated. Low-profile wire-based delivery systems were later developed to treat small diameter vessels not accessible by the traditional catheter delivery systems. Wire-based delivery systems generally include an elongate wire, such as a guidewire or hypotube, which has a distal segment configured to carry the prosthesis. A sheath, which may include a delivery catheter, is typically used to restrain the prosthesis on the wire and to assist in the delivery of the prosthesis to the treatment site. U.S. Pat. No. 6,989,024 entitled "Guidewire Loaded Stent for Delivery through a Catheter" discloses such a system.

The ability to accurately place the prosthesis at a treatment site is of paramount importance. Misplacement of the prosthesis will typically adversely impact the efficacy of the intended treatment and, in many instances, will require further patient treatment interventions. For this reason an ability to partially deploy the prosthesis to determine proper placement combined with an ability to return the prosthesis to its original unexpanded configuration, if the placement of the prosthesis is found to be incorrect, is highly desirable. Upon returning the prosthesis to its unexpanded state, the delivery system can be manipulated to place the prosthesis at the proper deployment location. A problem associated with returning the prosthesis to its unexpanded state is that the prosthesis tends to shift proximally on the delivery wire as a result of frictional forces acting on the prosthesis when it is withdrawn into the sheath.

U.S. Pat. No. 7,201,769 entitled "Expandable Stent and Delivery System" discloses a stent and delivery system that includes proximal, intermediate and distal cylindrical members disposed on and spaced apart along an elongated core member such that first and second gaps are formed. The expandable stent includes proximal and distal anchor members which align with the gaps. The expandable stent is mounted on the intermediate cylindrical member, and the anchor members, having a length slightly less than the length of the gaps, are disposed within the gaps thereby locking the stent onto the core member. Interlocking the proximal anchor members within the first gap locks the stent's position during resheathing. One problem with this delivery system is that it requires that gaps be formed on the wire between at least two cylindrical members for interlocking the anchor members. The delivery system also requires the use of an intermediate cylindrical member for mounting the stent. The need to orient at least two cylindrical members together to form each gap on the delivery wire creates design restrictions that can adversely impact delivery system characteristics, such as, for example, flexibility. Moreover, the required use of an intermediate cylindrical member for mounting the stent and for forming the gaps necessarily adds to the radial dimension of the delivery wire and affects its smallest achievable profile. The intermediate cylindrical member also impacts the flexibility of the distal segment of the delivery system by imposing additional stiffness.

SUMMARY OF THE DISCLOSURE

In accordance with one implementation there is provided a stent delivery system comprising an elongate flexible guide having a proximal section and a distal section, the distal section configured for mounting a stent and having a first radially extending member positioned proximal to a distal end of the elongate guide, the first radially extending member having a proximal side and a distal side, the stent mounted on the distal section of the elongate guide and having a body comprising proximal and distal ends, the stent having first and second locking members coupled to the proximal end of the stent body, the first locking member positioned on the proximal side of the first radially extending member, the second locking member positioned on the distal side of the first radially extending member; and a sheath disposed over at least a portion of the elongate guide to constrain the stent on the elongate guide.

In accordance with another implementation there is provided a stent delivery system comprising an elongate flexible guide having a proximal section and a distal section, the distal section configured for mounting a stent and having a first radially extending member positioned proximal to a distal end of the elongate guide, the first radially extending member having a proximal side and a distal side, the stent mounted on the distal section of the elongate guide and having a body comprising proximal and distal ends, the stent having a first locking member coupled to the proximal end of the stent body, the first locking member positioned on the proximal side of the first radially extending member, the proximal end of the stent body abutting or nearly abutting the distal side of the first radially extending member; and a sheath disposed over at least a portion of the elongate guide to constrain the stent on the elongate guide.

In accordance with yet another implementation there is provided a stent delivery system comprising an elongate flexible guide having a proximal section and a distal section, the distal section configured for mounting a stent and having a first radially extending member positioned proximal to a distal end of the elongate guide, the first radially extending member having a proximal side and a distal side, the stent mounted on the distal section of the elongate guide and having a body comprising proximal and distal ends, the proximal end of the stent body comprising struts, a first locking member and a second locking member positioned on one or more of the struts, the first locking member positioned on the proximal side of the first radially extending member, the second locking member positioned on the distal side of the first radially extending member; and a sheath disposed over at least a portion of the elongate guide to constrain the stent on the elongate guide.

In accordance with yet another implementation there is provided a stent delivery system comprising an elongate flexible guide having a proximal section and a distal section, the distal section configured for mounting a stent and having a first radially extending member positioned proximal to a distal end of the elongate guide, the first radially extending member having a proximal side and a distal side, the stent mounted on the distal section of the elongate guide and having a body comprising proximal and distal ends, the proximal end having a first locking member having first and second opposing surfaces, the first surface positioned on the proximal side of the radially extending member, the second surface positioned on the distal side of the radially extending member; and a sheath disposed over at least a portion of the elongate guide to constrain the stent on the elongate guide.

In accordance with another implementation there is provided a stent delivery system comprising an elongate flexible guide having a proximal section and a distal section, the distal section configured for mounting a stent and having a first radially extending member positioned proximal to a distal end of the elongate guide, the first radially extending member having a proximal side and a distal side, the stent mounted on the distal section of the elongate guide and having a longitudinal body comprising proximal and distal ends, a plurality of longitudinally offset first and second locking members extending from the proximal end of the stent body, the first locking members configured to engage a proximal side of the first axially extending member, the second locking member configured to engage a distal side of the first axially extending member; and a sheath disposed over at least a portion of the elongate guide to constrain the stent on the elongate guide.

BRIEF DESCRIPTION OF THE DRAWINGS

Preferred embodiments of the present disclosure are described herein with reference to the drawings wherein:

FIGS. 1A-1C illustrate a prosthesis and prosthesis delivery system in an embodiment of the present invention.

FIG. 2 illustrates a locking arrangement in an embodiment of the present invention.

FIGS. 4A-4C illustrate a prosthesis and prosthesis delivery system in another embodiment of the present invention.

FIG. 5 illustrates a locking arrangement in another embodiment of the present invention.

FIG. 6 illustrates an elongate guide in an embodiment of the present invention.

FIGS. 15A-15D illustrate a prosthesis and prosthesis delivery system in alternative embodiments of the present invention.

FIGS. 16A and 16B illustrate a prosthesis and prosthesis delivery system in another embodiment of the present invention.

FIGS. 17A and 17B illustrate a prosthesis and prosthesis delivery system in yet another embodiment of the present invention.

FIGS. 18A-C illustrate a prosthesis and prosthesis delivery system in alternative embodiments of the present invention.

FIGS. 19A and 19B illustrate a prosthesis and prosthesis delivery system in another embodiment of the present invention.

FIGS. 20A and 20B illustrate a prosthesis and prosthesis delivery system in yet another embodiment of the present invention.

FIGS. 22A and 22B illustrate a side and section view of a locking structure in another embodiment of the present invention.

FIG. 23 illustrates a locking structure in another embodiment of the present invention.

FIG. 24 illustrates a locking structure in another embodiment of the present invention.

FIGS. 26A-D illustrate a prosthesis and prosthesis delivery system in another embodiment of the present invention.

FIG. 33 illustrates a locking arrangement in an embodiment of the present invention.

FIG. 34 illustrates a locking arrangement in another embodiment of the present invention.

FIGS. 38A-E illustrate a prosthesis and alternative locking members in other embodiments of the present invention.

DETAILED DESCRIPTION

Figure 3:
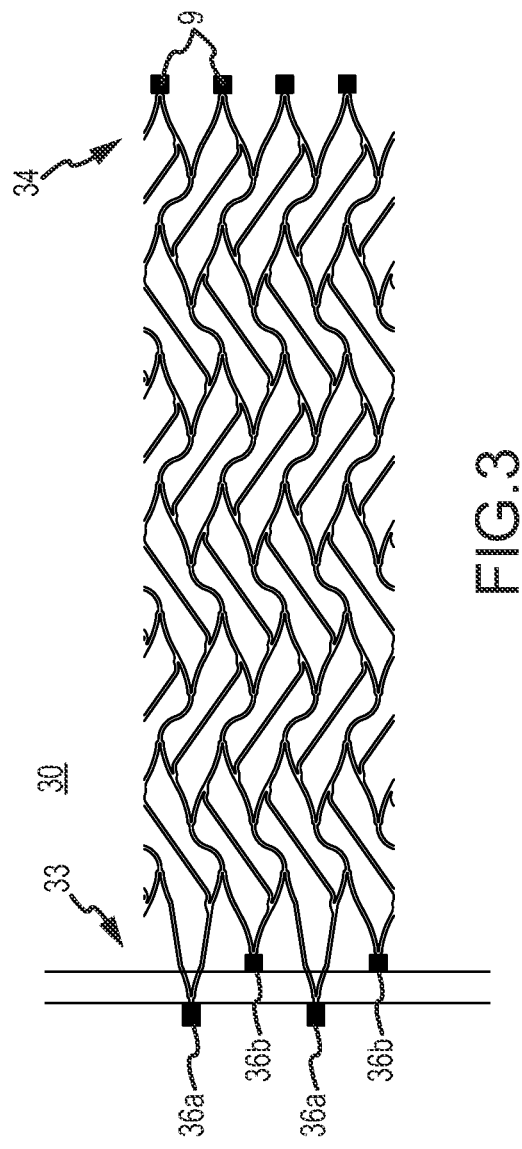
FIG. 3 illustrates a locking arrangement in another embodiment of the present invention.

FIGS. 1A, 1B and 1C illustrate a prosthesis delivery system in accordance with one embodiment of the present invention. The prosthesis delivery system 10 includes an elongate guide 12, such as, a guidewire, hypotube, or other elongate member, having a proximal segment 14 and a smaller diameter distal segment 16. A taper is generally provided on the wire as a transition between the larger diameter proximal segment 14 and the smaller diameter distal segment 16. The distal segment 16 of guide 12 includes a proximal coil segment 18 and a distal coil segment 22. The proximal coil segment 18 is positioned over at least a portion of the guide taper and is used to enhance the trackability of the guide as it is maneuvered through a delivery sheath, such as a catheter, as will be discussed in more detail below. The distal coil segment 22 located at the distal end 21 of guide 12 is typically formable to assist in steering the guide 12. Positioned or formed on the distal segment 16 of guide 12 is a radially extending member 19 having a proximal side 19a and a distal side 19b. Radially extending member 19 may comprise a coil, as shown, a cylindrical member or a host of other geometric configurations which are discussed in more detail later in the description. In one embodiment, radially extending member 19 is coated with or comprises a radiopaque material.

Positioned on the distal segment 16 of guide 12 is a radially self-expanding prosthesis 30 that is preferably made of shape memory material, such as Nitinol. In FIG. 1C, as with many of the drawings in the present application, the prosthesis and radially extending member are illustrated in a plain view as if the devices were cut and laid flat on a surface. Elongate guide features other than the radially extending member have also been omitted. This has been done to more particularly demonstrate the features of the prosthesis and their interaction with the radially extending member. With continued reference to FIG. 1C, prosthesis 30 includes a longitudinal body portion 32 having a proximal end 33 and a distal end 34. The proximal end 33 of the prosthesis has a set of longitudinally offset locking members 36a and 36b with locking members 36a positioned proximal to locking members 36b. When positioned on the guide 12, the longitudinal body portion 32 of prosthesis 30 resides, or substantially resides, distal to radially extending member 19 with locking members 36a residing on the proximal side 19a of member 19 and locking members 36b residing on the distal side 19b of member 19. In a preferred embodiment the distal ends 37 of locking members 36a abut the proximal side 19a of member 19 and the proximal ends 39 of locking members 36b abut the distal side 19b of member 19. In other embodiments, one or both of locking members 36a and 36b is placed in close proximity to the radially extending member 19 without abutting it. Preferably, one or more of locking members 36a and 36b is coated or made of a radiopaque material, such as tungsten, platinum, platinum/iridium and gold. In other embodiments, one or more of locking members 36a and 36b comprise a bioabsorbable material. Locking members 36a and 36b may comprise any of a variety of structures such as, for example, coils, cylindrical elements, rectangular blocks or other structures which are discussed in more detail later in the description. It is important to note that the locking members 36a and 36b need not have a uniform outer dimension or profile. For example, in alternative embodiments the ends of the locking members that abut radially extending member 19 are dimensionally larger than other parts of the locking members. In one embodiment, one or both of locking members 36a and 36b comprise elements that have been crimped to create a non-uniform outer profile, such as a dog-bone configuration.

In practice, the prosthesis 30 may be carried by the elongate guide 12 to a treatment site within a patient by a variety of means. One method includes positioning a distal end of a catheter at the treatment site and subsequently advancing the elongate guide 12 that carries the prosthesis 30 through a lumen of the catheter to the treatment site. The catheter may be, for example, a micro-catheter, infusion catheter, angioplasty catheter, or any other catheter having a lumen sufficient for receiving the elongate guide 12 and prosthesis 30. The lumen for receiving the elongate guide 12 and prosthesis 30 may be a guidewire lumen that forms a part of the catheter. Another method includes positioning the elongate guide 12 that carries the prosthesis 30 into a lumen of a delivery catheter and subsequently delivering the guide and catheter as a unit to the treatment site. Another method includes providing a retractable sheath over the distal segment 16 of guide 12 to restrain the prosthesis 30 on the guide. In such an embodiment, the prosthesis 30 may be delivered on the guide 12 without the use of a delivery catheter. In yet another embodiment, a sheathed delivery system as just discussed may be delivered through the lumen of a catheter whose distal end has been previously placed at or near the treatment site. In each of these aforementioned delivery methods it is important that the longitudinal position of the prosthesis on the elongate guide be properly maintained during the delivery process. And, as previously discussed, an ability to partially deploy the prosthesis to determine proper placement combined with an ability to return the prosthesis to its original unexpanded configuration, if the placement of the prosthesis is found to be incorrect, is highly desirable.

In the embodiment of FIG. 1A, the prosthesis delivery system 10 includes a catheter 40 having an internal lumen 42 that contains the elongate guide 12 and prosthesis 30. In the embodiment shown, catheter 40 is used to carry the guide 12 and prosthesis 30 to the treatment site and also acts to restrain the prosthesis 30 on the distal segment of the elongate guide. A radiopaque marker 44 may be provided at or near the distal end of catheter 40. The dimensional relationship between lumen 42 and the components of guide 12 and prosthesis 30 cause the locking members 36a and 36b to engage with radially extending member 19 in a manner that locks the proximal end 33 of prosthesis 30 on the guide while permitting a sliding relationship between the catheter and elongate guide. Locking the proximal end 33 of the prosthesis on the guide enables the prosthesis to be partially deployed/expanded without slipping off the guide and further enables the prosthesis to be repositioned to its unexpanded state within the catheter.

An advantage of the delivery system 10, and other embodiments disclosed herein, is that the longitudinal position of the prosthesis 30 on the guide 12 may be fixed or controlled by the use of a single radially extending member 19. This is accomplished by providing features on the prosthesis 30 that are configured to engage with the proximal and distal sides 19a and 19b of the radially extending member 19 to lock or limit movement of the proximal end 33 of the prosthesis 30 on the elongate guide 12 when positioned within a sheath and/or delivery catheter 40. In addition, this locking technique provides the "push" and "pull" capabilities necessary for deploying and resheathing the prosthesis 30. In other words, when the prosthesis 30 is moved out of the catheter 40 by advancing the guide 12 and/or retracting the catheter 40, the proximal ends 39 of locking members 36b will engage the distal side 19b of member 19 to provide the "push" required for advancing the prosthesis 30 through the catheter 40. In cases where it is necessary to retract the prosthesis 30 back into the catheter 40, a "pull" force is provided by the engagement of the distal ends 37 of locking members 36a with the proximal side 19a of member 19. Another advantage is that the staggered arrangement of locking member 36a and 36b results in a more controlled release of the proximal end 33 of the prosthesis 30. This is accomplished by the release of locking members 36b prior to the release of locking members 36a.

In the embodiments of FIGS. 1A and 1C, the proximal end 33 of prosthesis 30 comprises a plurality of struts that form short peak segments 31 and long peak segments 35. Moreover, each of the peak segments possesses a locking member 36a or 36b. In situations where visualization of the proximal end of the prosthesis is important, providing a radiopaque locking member on each peak segment is desirable. However, in other circumstances where the locking members are not needed to enhance the visibility of the prosthesis and/or fewer locking members are needed to lock the proximal end of the prosthesis onto the guide, less than all of the peak segments may possess a locking member. For example, in one embodiment prosthesis 30 includes only one of each locking member 36a and 36b, as shown in FIG. 2. Further, in alternative embodiments a cylindrical member (not shown), such as a coil segment, is provided on the elongate guide 12 for mounting the prosthesis 30.

In the embodiment of FIG. 3, radiopaque markers 9 are also provided at the distal end 34 of prosthesis 30 to enhance visibility of the distal end of the prosthesis as it is delivered and placed at a treatment site.

In exemplary embodiments, the proximal segment 14 of elongate guide has an outer diameter of about 0.002 inches and about 0.020 inches, and preferably between about 0.010 inches and about 0.016 inches. The distal segment 16 has an outer diameter of about 0.002 inches and about 0.020 inches, and preferably between about 0.003 inches and about 0.006 inches. Radially extending member 19 has a length of between about 0.1 mm and about 0.75 mm, and preferably about 0.40 mm and outer diameter of between about 0.006 inches and about 0.023 inches, and preferably between about 0.010 inches and about 0.0165 inches.

Figure 7:
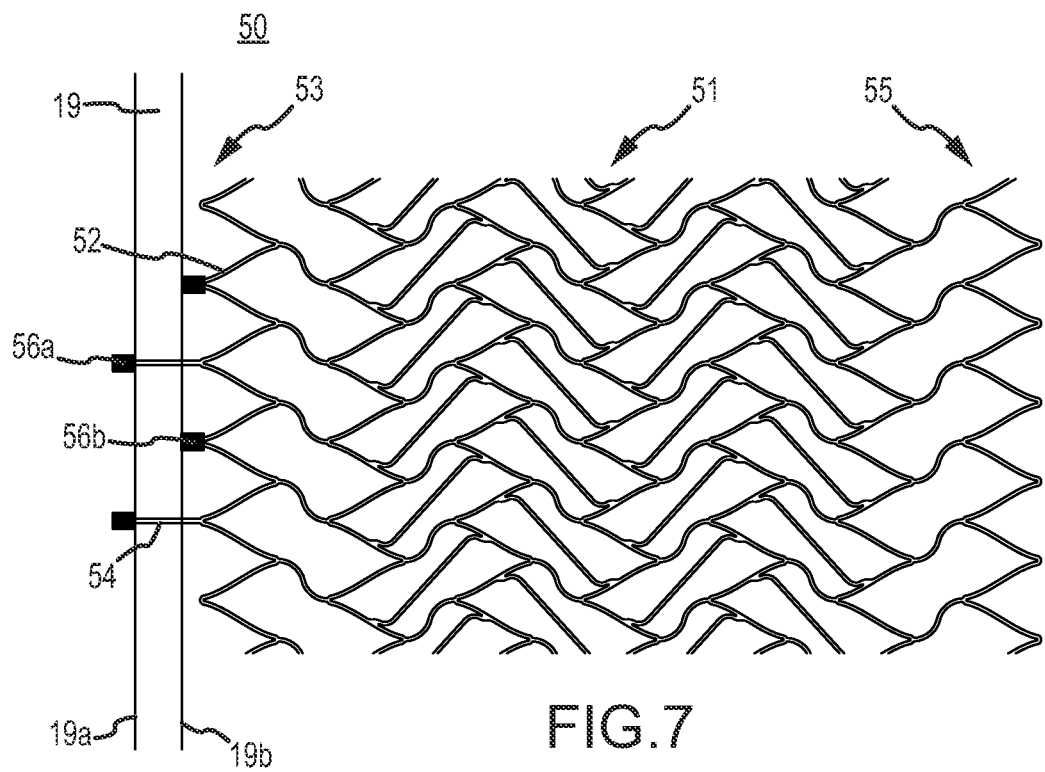
FIG. 7 illustrates a locking arrangement in an embodiment of the present invention.
Figure 8:
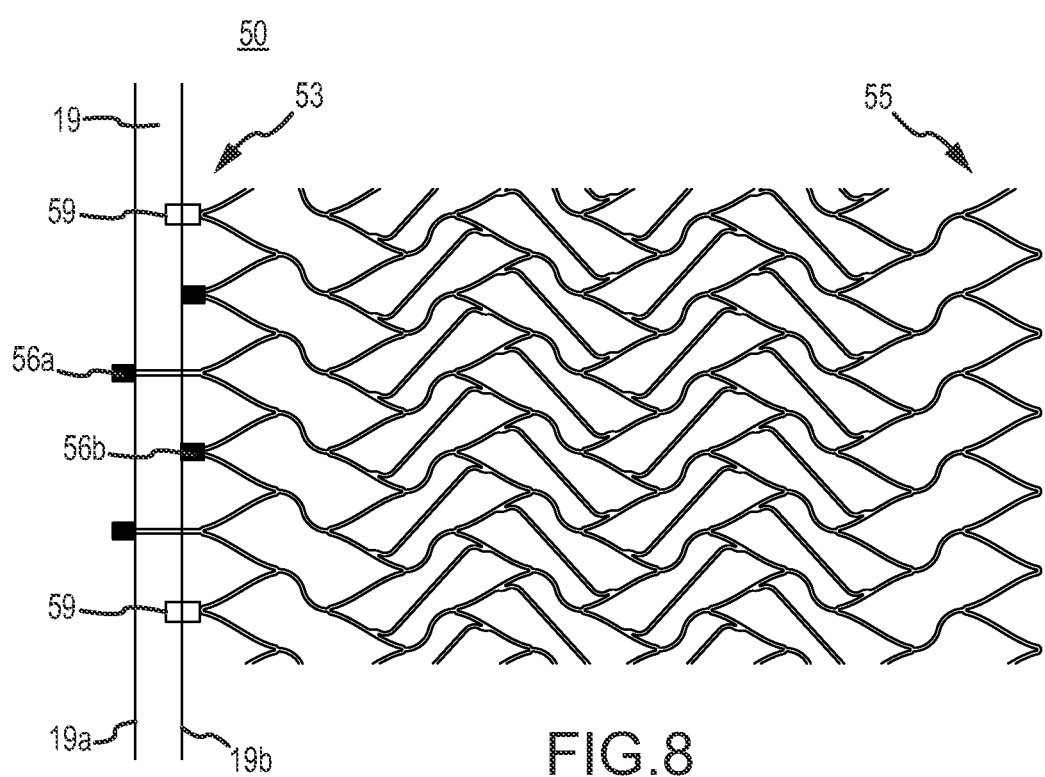
FIG. 8 illustrates a locking arrangement in another embodiment of the present invention.

With reference to FIG. 7, a locking arrangement of a delivery system in another embodiment of the present invention is shown. The delivery system includes a prosthesis 50 with a longitudinal body portion 51 having proximal and distal ends 53 and 55, respectively, with the ends of the prosthesis comprising a plurality of substantially uniform peak portions 52. Longitudinally offset locking members 56a and 56b are also provided to engage with the proximal and distal sides 19a and 19b of radially extending member 19. The longitudinal offset of the locking members is accomplished by attaching locking members 56a to legs 54 that extend from some of the peak portions 52 and by attaching locking members 56b to the peak portions themselves. In the embodiment of FIG. 8, prosthesis 50 includes one or more additional features 59 that are attached to some of the peak portions 52. Features 59 may comprise, for instance, radiopaque markers when locking members 56a and 56b are not used as markers. Additional radiopaque markers (not shown) may also be provided on the distal end 55 of the prosthesis 50. Features 59 may also comprise members that are positioned to reside on the outer surface of the radially extending member and dimensioned to assist in maintaining alignment of the proximal end 53 of the prosthesis with the radially extending member 19 during delivery and/or deployment of the prosthesis 50. In one embodiment, features 59 are drug delivery devices that are configured to dispense or elute a therapeutic agent at the patient treatment site. In one embodiment, features 59 comprise a polymer matrix containing the therapeutic agent. The polymer matrix may comprise a bioabsorbable polymer.

Before moving on, it is important to note that the embodiments of FIGS. 1A, 1B and 1C, nor any of the embodiments disclosed herein, is restricted to the use of a delivery catheter or to any other particular delivery method. In use, all that is needed is a member that is capable of restraining the prosthesis 30 on the guide 12 in a manner that causes locking members 36a and 36b to be properly positioned with respect to radially extending member 19, and that relative movement between the member and guide 12 permits deployment of the prosthesis. Moreover, it is important to note that the present invention is not limited to any particular elongate guide construction. All that is needed is a guide construction that includes one or more radially extending members that are capable of cooperating with locking members on the prosthesis as taught herein. The elongate guide may include a solid or hollow structure, or a combination thereof, comprising a metal, polymer, composite or any other material suitable for carrying a prosthesis to a treatment site located within a duct of a patient (e.g., vasculature, urinary tract, etc.).

Figure 4A:
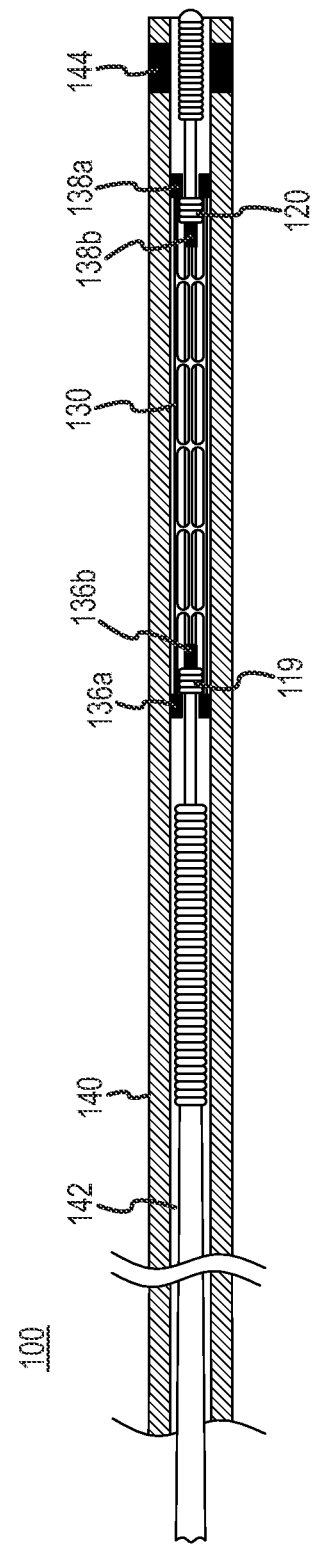

With reference to FIGS. 4A, 4B and 4C, a prosthesis delivery system 100 of another embodiment is shown. Delivery system 100 is similar to the delivery system 10 of FIGS. 1A, 1B and 1C except that the elongate guide 112 has two radially extending members 119 and 120 located on a distal segment 116 thereof. In addition, prosthesis 130 includes two sets of locking members 136 and 138 that are configured to respectively cooperate with radially extending members 119 and 120 so as to lock the longitudinal position or control the longitudinal movement of the prosthesis 130 with respect to the elongate guide 112.

Prosthesis delivery system 100 includes an elongate guide 112 having a proximal segment 114 and a smaller diameter distal segment 116. A taper is generally provided on the wire as a transition between the larger diameter proximal segment 114 and the smaller diameter distal segment 116. The distal segment includes a proximal coil segment 118 and a distal coil segment 122. Positioned or formed on the distal segment 116 of guide 112 is a first radially extending member 119 having a proximal side 119a and a distal side 119b and a second radially extending member 120 having a proximal side 120a and a distal side 120b. Radially extending members 119 and 120 may comprise coils, as shown, cylindrical members (as shown in FIG. 6) or other geometric configurations that are discussed in more detail later in the description. In one embodiment, one or both of radially extending members 119 and 120 are coated with or comprise a radiopaque material.

Positioned on the distal segment 116 of guide 112 is a radially self-expanding prosthesis 130. Prosthesis 130 includes a longitudinal body portion 132 having a proximal end 133 and a distal end 134. The proximal end 133 of the prosthesis has a set of longitudinally offset locking members 136. As shown in FIG. 4C, the proximal set of locking members 136 include locking members 136a and 136b with locking members 136a positioned proximal to locking members 136b. Likewise, the distal set of locking members 138 include locking members 138a and 138b with locking members 138a positioned distal to locking members 138b. When positioned on the guide 112, the longitudinal body portion 132 of prosthesis 130 resides between the first and second radially extending members 119 and 120 with locking members 136a residing on the proximal side 119a of member 119, locking members 136b residing on the distal side 119b of member 119, locking members 138a residing on the distal side 120b of member 120 and locking members 138b residing on the proximal side 120a of member 120. In practice, prosthesis 130 may be carried by the elongate guide 112 to a treatment site within a patient by a variety of means as previously discussed.

In the embodiment of FIG. 4A, the prosthesis delivery system 100 includes a catheter 140 having an internal lumen 142 that contains the elongate guide 112 and prosthesis 130. In the embodiment shown, catheter 140 is used carry the guide 112 and prosthesis 130 to the treatment site and also acts to restrain the prosthesis 130 on the distal segment of the elongate guide. The dimensional relationship between lumen 142 and the components of guide 112 and prosthesis 130 cause the locking members 136 and 138 to cooperate with the radially extending members 119 and 120 in a manner that locks the longitudinal position, or inhibits longitudinal movement, of the prosthesis on the guide while permitting a sliding relationship between the catheter and elongate guide. An advantage of the delivery system 100 is that the longitudinal position of the prosthesis 130 on the guide 112 may be fixed or controlled by the use of the longitudinally offset locking members 136 and 138 located at opposing ends of the prosthesis 130 which are configured to respectively cooperate with radially extending member 119 and 120 located on the elongate guide 112.

In the embodiments of FIGS. 4A and 4C, the proximal and distal ends 133 and 134 of prosthesis 130 each comprise a plurality of struts that form short peak segments 131 and long peak segments 135. Moreover, each of the peak segments 131 and 135 includes a locking member 136 or 138. In situations where visualization of the proximal and distal ends of the prosthesis is important, providing a radiopaque locking member on each peak segment is desirable. However, in other circumstances where the locking members are not needed to enhance the visibility of the prosthesis, less than all of the peak segments may include a locking member. For example, in one embodiment prosthesis 130 includes only one of each locking member 136a, 136b, 138a and 138b as shown in FIG. 5.

Figure 9:
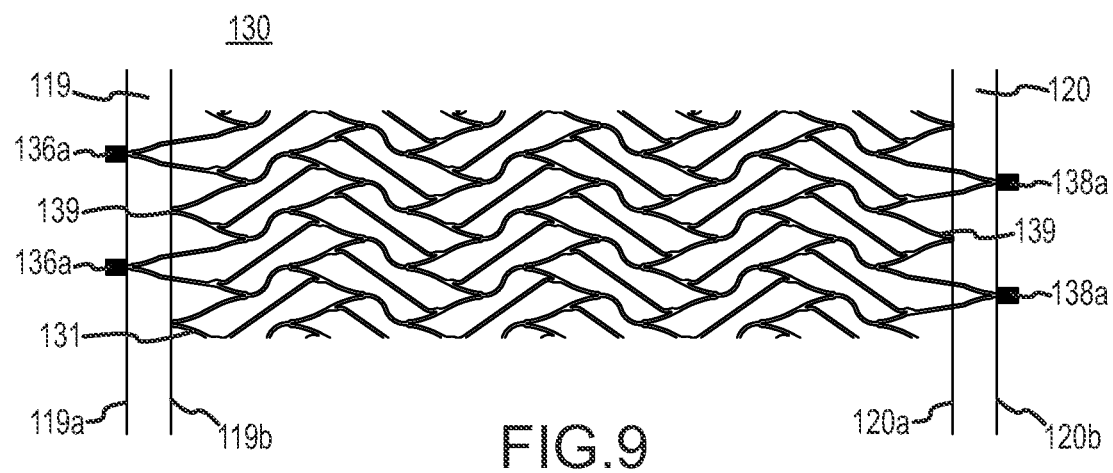
FIG. 9 illustrates a locking arrangement in yet another embodiment of the present invention.

FIG. 9 shows a modified version of prosthesis 130 whereby locking members 136b and 138b are omitted from the short peak segments 131 of the prosthesis. Instead of using locking members 136b and 138b to abut the respective inside surfaces 119b and 120a of radially extending members 119 and 120, the apexes 139 of the short peaks 131 themselves are used. In alternative embodiments, the short peak segments 131 are strengthened by making their struts wider and/or thicker than the other prosthesis strut members (not shown).

Figure 10:
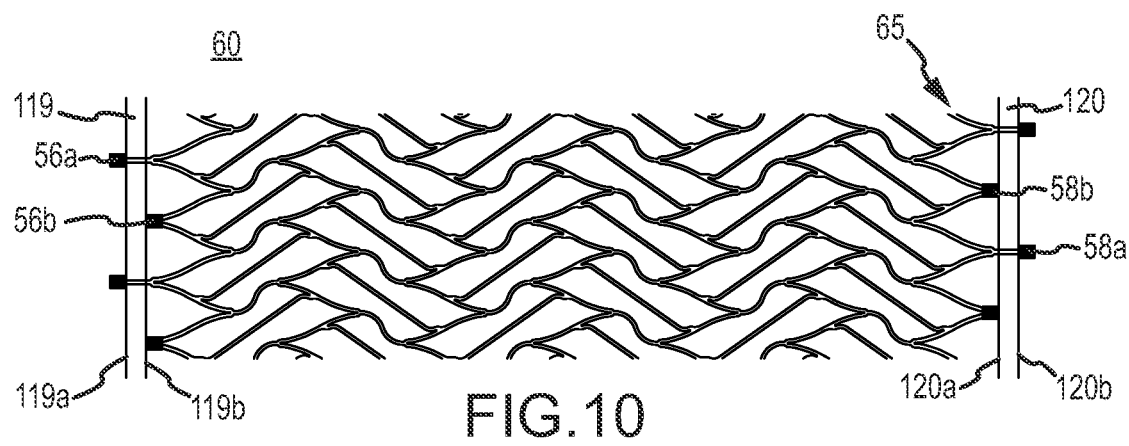
FIG. 10 illustrates a locking arrangement in an embodiment of the present invention.
Figure 11:
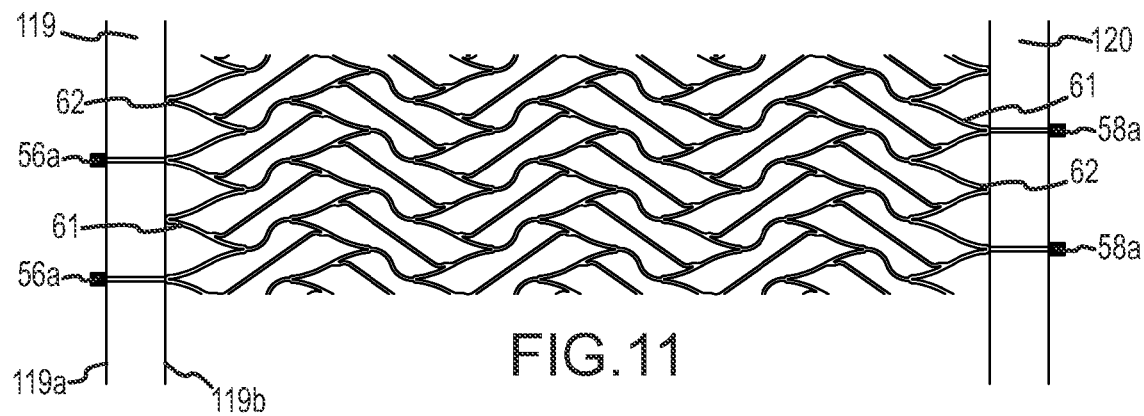
FIG. 11 illustrates a locking arrangement in another embodiment of the present invention.

In the implementation of FIG. 10, prosthesis 60 has a configuration similar to prosthesis 50 discussed above in conjunction with FIG. 7 except that it also includes locking members 58a and 58b at its distal end 65 for engaging radially extending member 120. In the embodiment of FIG. 11, prosthesis 60 is modified by the omission of locking members 56b and 58b. Instead of using locking members 56b and 58b to abut the respective inside surfaces 119b and 120a of radially extending members 119 and 120, the apexes 62 of at least some of the end peaks 61 themselves provide the abutment means. In alternative embodiments, some or all of the struts forming the end peaks 62 that abut the inside surfaces 119b and 120a of members 119 and 120 are made wider and/or thicker to strengthen the abutting end peaks.

Figure 12:
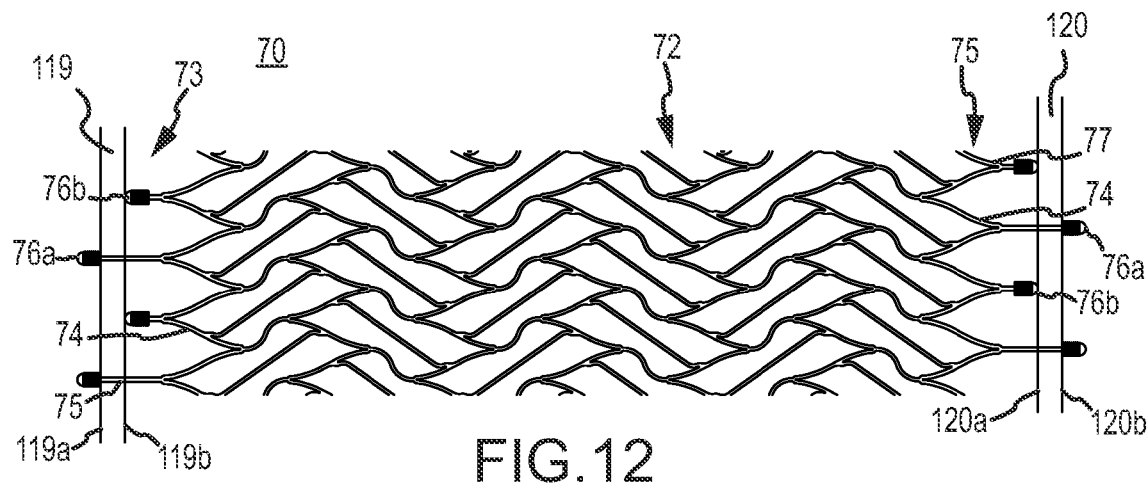
FIG. 12 illustrates a locking arrangement in yet another embodiment of the present invention.

In the implementation of FIG. 12, a prosthesis 70 is shown in a locked position with respect to radially extending members 119 and 120. Prosthesis 70 includes a longitudinal body portion 72 having proximal and distal ends 73 and 75, respectively. Each end of the prosthesis comprises strut segments that are interconnected to form peak segments 74. In the embodiment of FIG. 12, half of the peak segments have long legs/extensions 75 extending therefrom, while the other half of the peak segments have short legs/extensions 77 extending therefrom. Attached or formed on the long extensions 75 are locking members 76a which are configured to engage the outside surfaces 119a and 120b of radially extending members 119 and 120. Attached or formed on the short extensions 77 are locking members 76b which are configured to engage the inside surfaces 119b and 120a of radially extending members 119 and 120. In FIG. 12, locking members 76a and 76b comprise coils, and preferably radiopaque coils. It is appreciated, however, that the locking members may comprise any of a variety of structures other than cylindrical forms, as is the case with any of the embodiments disclosed herein.

Figure 13:
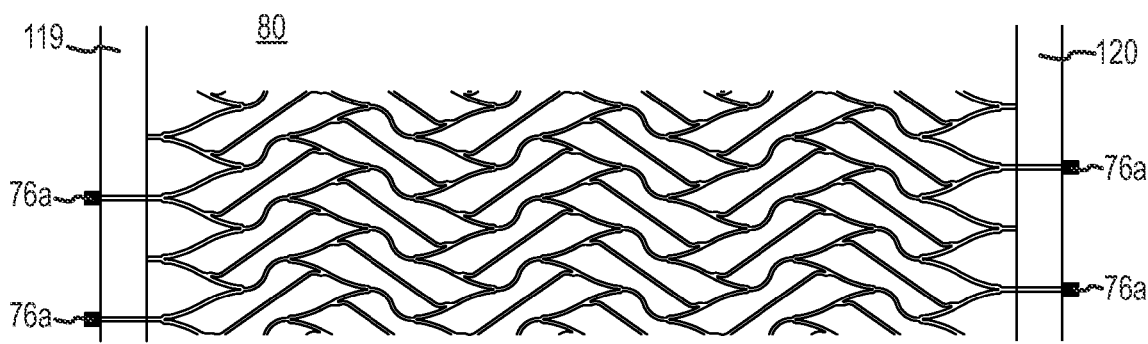
FIG. 13 illustrates a locking arrangement in an embodiment of the present invention.

In the implementation of FIG. 13, a prosthesis 80 is shown in a locked position with respect to radially extending members 119 and 120. Prosthesis 80 is a modification of the prosthesis 70 shown in FIG. 12, the modification being the omission of locking members 76b from short extensions 77. Instead of using locking members 76b to abut the respective inside surfaces 119b and 120a of radially extending members 119 and 120, the ends of the short extensions themselves provide the abutment means. In an alternative embodiment, the short extensions 77 are strengthened by making them wider and/or thicker than the long extensions 75.

Figure 45:
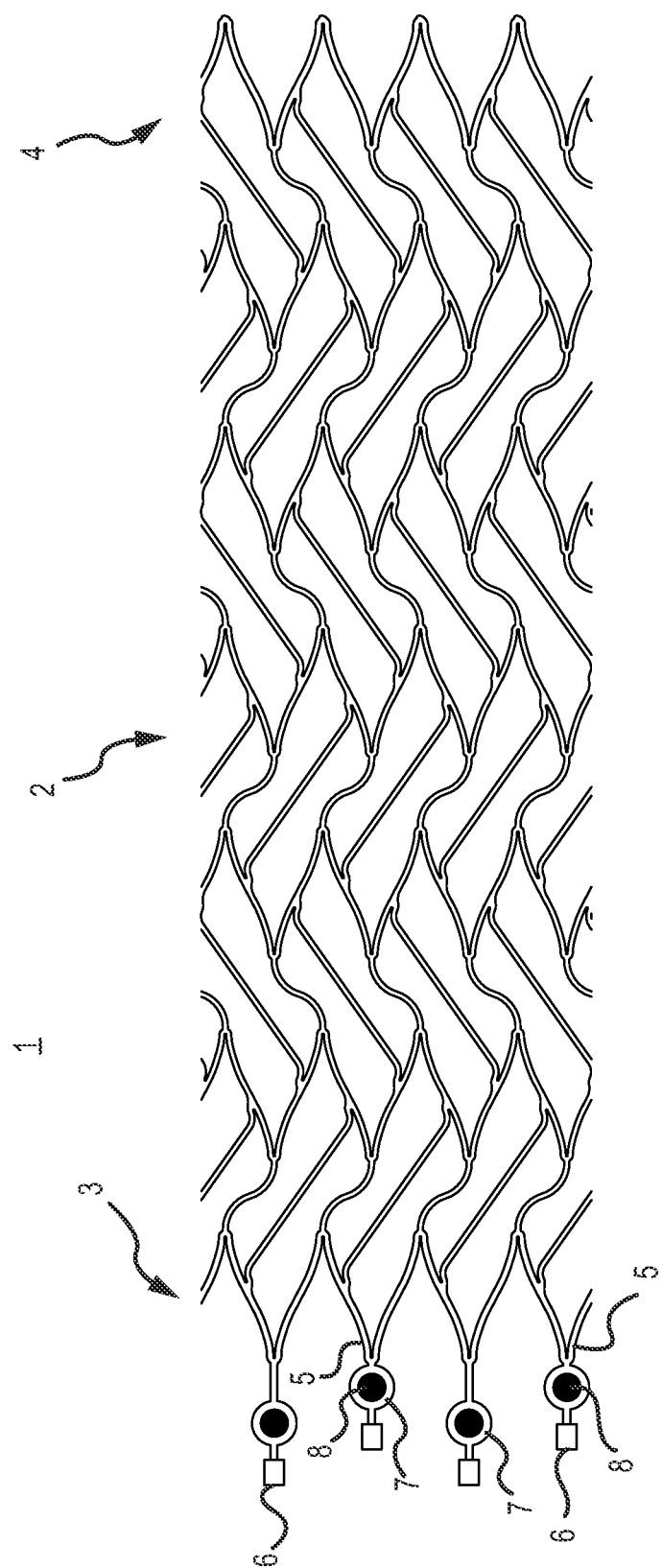
FIG. 45 illustrates a prosthesis in an embodiment of the present invention.

FIG. 45 shows a prosthesis 1 in another embodiment of the present invention. Prosthesis 1 includes a longitudinal body portion 2 having proximal and distal ends 3 and 4, respectively. The proximal end 3 of the prosthesis comprises strut segments that are interconnected to form peak segments 5. Attached to the peak segments 5 are locking members 6 which are arranged in a staggered configuration similar to what has been described in previous embodiments. Positioned between the peak segments 5 and locking members 6 are slotted features 7 that have located within them radiopaque markers 8. In a preferred embodiment, locking members 6 comprise the same material used in the construction of the body 2 of the prosthesis 1, but may comprise other materials.

Figure 14:
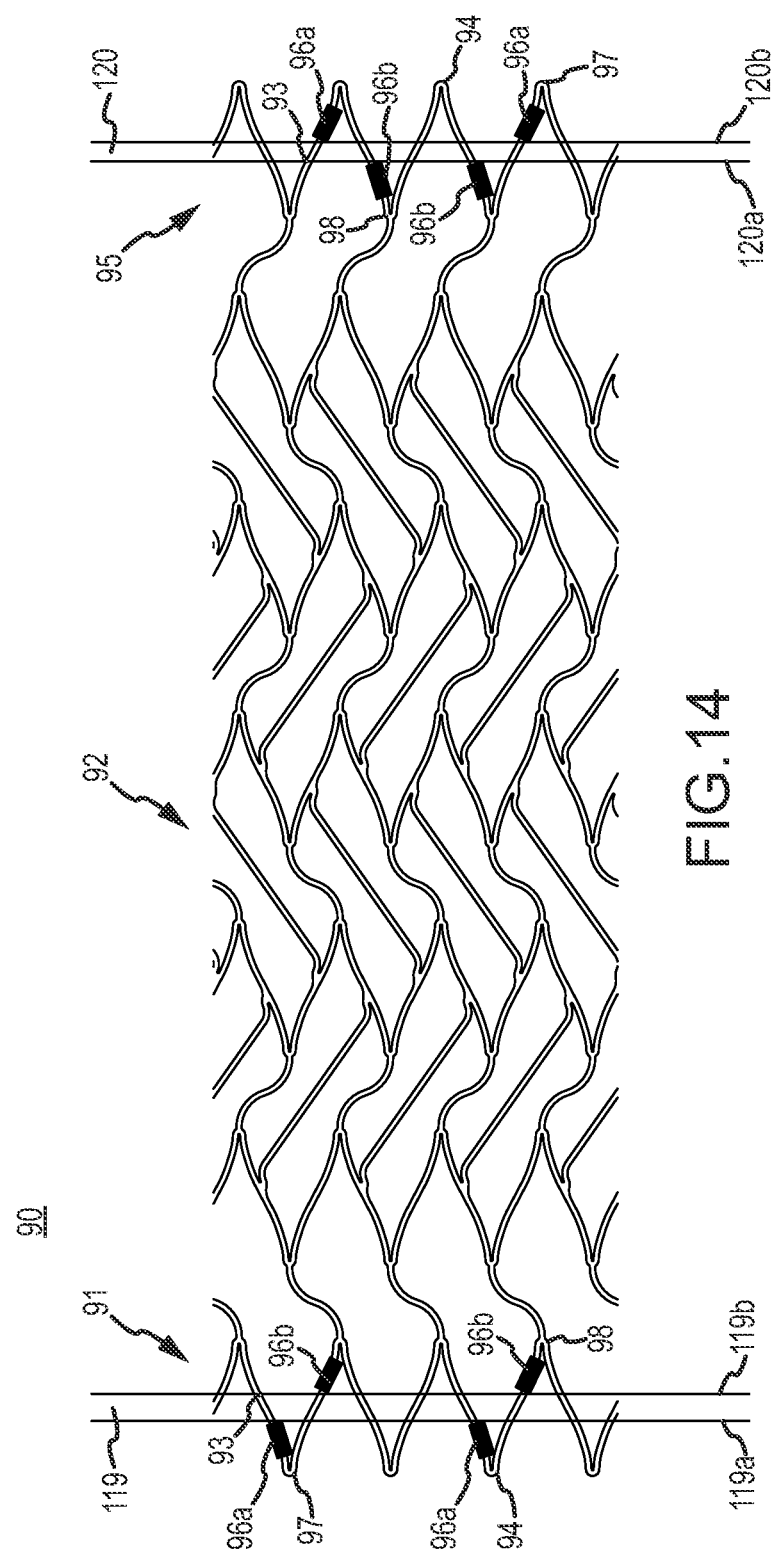
FIG. 14 illustrates a locking arrangement in another embodiment of the present invention.

In the implementation of FIG. 14, prosthesis 90 is shown in a locked position with respect to radially extending members 119 and 120. Prosthesis 90 includes a longitudinal body portion 92 having a proximal end 91 and a distal end 95. Each of the proximal and distal ends comprise undulating struts 93 and 94 that are connected to form peak portions 97 and valley portions 98. At least some of the struts 93 and 94 have locking members 96a and 96b which are positioned and configured to engage opposite sides of radially extending members 119 and 120. Locking members 96a are generally positioned on struts 93 near the peak portions 97 so that they abut, or nearly abut, the outside surfaces 119a and 120b of radially extending members 119 and 120. Locking members 96b are generally positioned on struts 94 near the valley portions 98 so that they abut, or nearly abut, the inside surfaces 119b and 120a of radially extending members 119 and 120. In one embodiment, locking members 96a and 96b comprise radiopaque metallic cylinders that are soldered onto the struts.

Figure 15C:
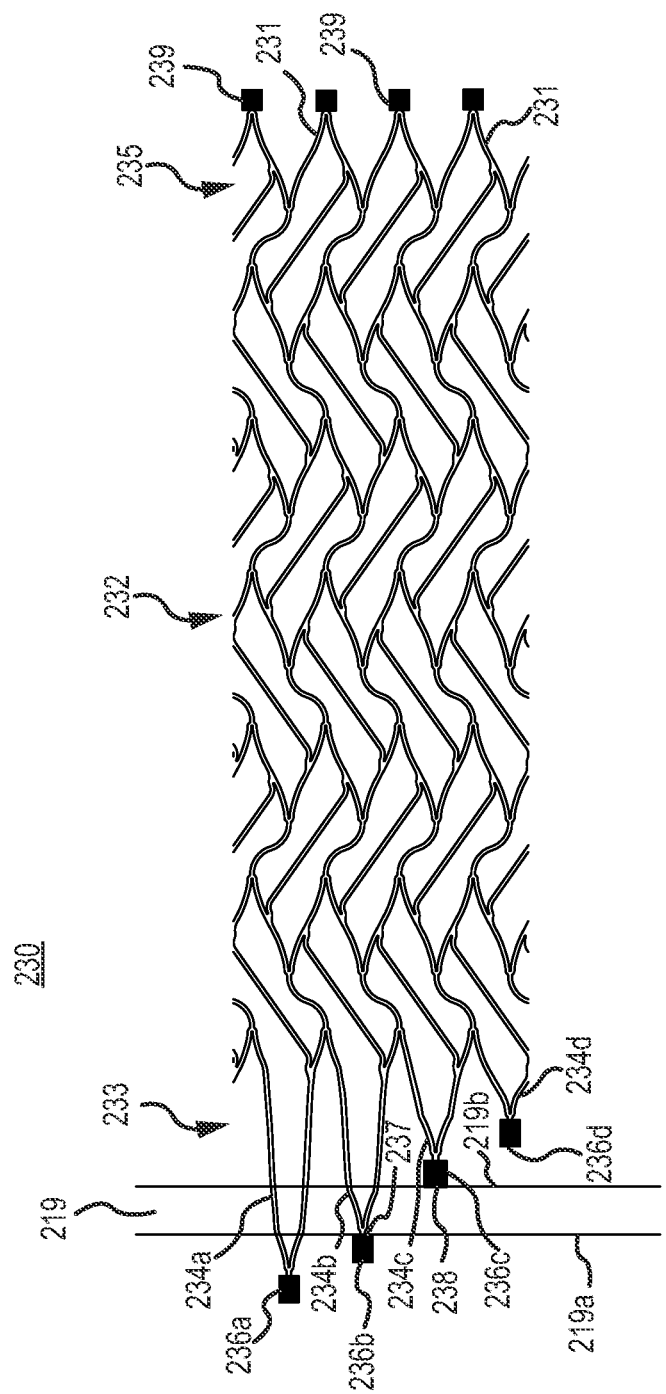

A problem generally associated with deploying a self-expanding prosthesis is that when the proximal end of the prosthesis is released, the prosthesis tends to "jump" to its fully deployed positioned. The abrupt expansion or "jumping" of the prosthesis to its fully expanded position tends to cause the prosthesis to move within the vessel and can result in an improper placement of the prosthesis. Certain embodiments of the present invention address this problem with the use of an arrangement of longitudinally offset/staggered locking members. FIGS. 15A, 15B and 15C illustrate a prosthesis delivery system in accordance with another embodiment that provides a controlled release of the proximal end of the prosthesis in order to avoid the aforementioned "jumping" problem. The prosthesis delivery system 200 includes an elongate guide 212, such as, a guidewire, hypotube, or other elongate member, having a proximal segment 214 and a smaller diameter distal segment 216. A taper 217 on the guide provides a transition between the larger diameter proximal segment 214 and the smaller diameter distal segment 216.

Guide 212 may also include a coil (not shown) that is positioned over at least a portion of the taper 217. The distal segment 216 of guide 212 includes a distal coil segment 222 located at the distal end 221 of guide 212. Positioned or formed on the distal segment 216 of guide 212 is a radially extending member 219 having a proximal side 219a and a distal side 219b. Radially extending member 219 may comprise a coil, as shown, a cylindrical member or a host of other geometric configurations which are discussed in more detail later in the description. In one embodiment, radially extending member 219 is coated with or comprises a radiopaque material.

Positioned on the distal segment 216 of guide 212 is a radially self-expanding prosthesis 230. Prosthesis 230 includes a longitudinal body portion 232 having a proximal end 233 and a distal end 235. The proximal end 233 of the prosthesis has a set of locking members 236a-d. Each of the locking members 236a-d are longitudinally offset one from the others with locking member 236b position distal to locking member 236a, locking member 236c located distal to locking member 236b, and locking member 236d located distal to locking member 236c. In the embodiment of FIG. 15C, the proximal end 233 of the prosthesis comprises a plurality of peak segments 234a-d having apexes that are longitudinally offset from one another in a staggered configuration. Each of locking members 236a-d are located at the apex of corresponding peak segments 234a-d. When prosthesis 230 is positioned on the guide 212, locking members 236a and 236b are positioned on the proximal side 219a of radially extending member 219 with locking member 236a spaced proximally from member 219 and locking member 236b abutting, or nearly abutting, the proximal side 219a of member 219. Locking members 236c and 236d are positioned on the distal side 219b of radially extending member 219 with locking member 236d spaced distally from member 219 and locking member 236c abutting, or nearly abutting, the distal side 219b of member 219. In the embodiment of FIG. 15C, the distal end 235 of prosthesis 230 includes a plurality of uniform peak segments 231 having radiopaque markers 239 attached at their apexes. Preferably, one or more of locking members 236a-d is coated with or made of a radiopaque material. In other embodiments, one or more of locking members 236a-d comprises a bioabsorbable material.

In the embodiment of FIG. 15A, the prosthesis delivery system 200 includes a catheter 240 having an internal lumen 242 that contains the elongate guide 212 and prosthesis 230. In the embodiment shown, catheter 240 is used to carry the guide 212 and prosthesis 230 to the treatment site and also acts to restrain the prosthesis 230 on the distal segment of the elongate guide. A radiopaque marker 244 may be provided at or near the distal end of catheter 240. The dimensional relationship between lumen 242 and the components of guide 212 and prosthesis 230 cause the locking members 236b and 236c to be positioned to engage with radially extending member 219 and also cause locking members 236a and 236d to be wedged between the inner wall of catheter 242 and elongate guide 212. In combination, locking members 236a-d function to lock the proximal end 233 of prosthesis 230 in a fixed position on guide 212 and also provide a controlled release of the proximal end of the prosthesis during deployment. In one embodiment, locking members 236a and 236d have larger dimensional characteristics than locking members 236b and 236c to facilitate wedging of the members between the delivery catheter 240 and elongate guide 212.

As discussed in earlier embodiments, deployment of a self-expanding prosthesis from its unexpanded state to its fully deployed and expanded state generally includes moving the prosthesis out of its delivery catheter by advancing the guide that carries the prosthesis and/or retracting the catheter. In the embodiment of FIG. 15A, a controlled release of the proximal end 233 of prosthesis 230 is achieved by a sequential release of locking members 236a-d in a distal to proximal manner. That is, locking member 236d is released first followed by member 236c which is followed by member 236b which is followed lastly by member 236a. The sequential and gradual release of the proximal end of the prosthesis minimizes or eliminates altogether the "jumping" phenomenon discussed above.

In the embodiments of FIGS. 15A and 15C, staggering of locking members 236a-d is achieved by attaching them to staggered peak segments 234a-d formed on the prosthesis 230. It is appreciated that this aspect of the invention is not limited to any particular prosthesis configuration nor is it limited to the use of only four locking members. For example, as few as two locking members may be used. All that is needed is a prosthesis that facilitates a sequential longitudinal offsetting of at least some of the locking members at the proximal end of the prosthesis. This may be achieved, for example, with the use of legs of varying length extending longitudinally from the proximal end of the prosthesis. In an alternative embodiment, as shown in FIG. 15D, two spaced-apart radially extending members 219 and 220 are positioned on the elongate guide to engage with the staggered locking members 236a-d. As shown, locking members 236a and 236b are positioned on opposite sides of radially extending member 219 and locking members 236c and 236d are positioned on opposite sides of radially extending member 220, as shown in FIG. 15D.

FIGS. 16A and 16B illustrate a delivery system 250 in another embodiment of the invention which is similar in construction to the embodiment of FIG. 6 above except for the structure of the radially extending members 70 and 72. The first radial extending member 70 includes a proximal side 70a and a distal side 70b and has ledges 71a and 71b located on each of the sides. Ledges 71a and 71b reside some distance above elongate guide 80. In a like manner, second radial extending member 72 includes a proximal side 72a and a distal side 72b and has ledges 73a and 73b. A prosthesis 84 positioned on the elongate guide 80 has at each of its ends a set of locking members 86a and 86b that engage with radially extending members 70 and 72 to lock or limit movement of the prosthesis while it is being delivered to a treatment site. As shown, a part of each locking members rests on a ledge of one of the radially extending members 70 and 72. An advantage of this configuration is that it promotes wedging of the locking members 86a and 86b between the inner wall 92 of catheter 90 and the distal segment 82 of guide 80. Wedging of locking members 86a and 86b enhances their locking capability. As a result, fewer locking members may be used without compromising securement of the prosthesis. In an alternative embodiment, only the proximal radially extending member 70 is provided. In such an embodiment, locking members 86a and 86b need only be provided on the proximal end of prosthesis 84. In another embodiment, one or both of locking members 70 and 72 include a ledge on only one of their sides.

FIGS. 17A and 17B illustrate a delivery system similar to the delivery system of FIGS. 4A and 4B except that the proximal and distal radially extending members 119 and 120 have outer dimensions different from one another. In the embodiment of FIGS. 17A and 17B, the proximal radially extending member 119 has a greater outer dimension than the distal radially extending member 120. As a result, the proximal locking members 136 on prosthesis 130 may have a smaller outer dimension than the distal locking members 138.

In an alternative embodiment, radially extending member 120 has an outer dimension greater than radially extending member 119. An advantage of having radially extending members of different dimensions is that the locking characteristic at each end of the prosthesis can be made to be different from one another. For example, the proximal end of the prosthesis can be made to be more firmly secured to the elongate guide than its distal end.

Figure 21A:
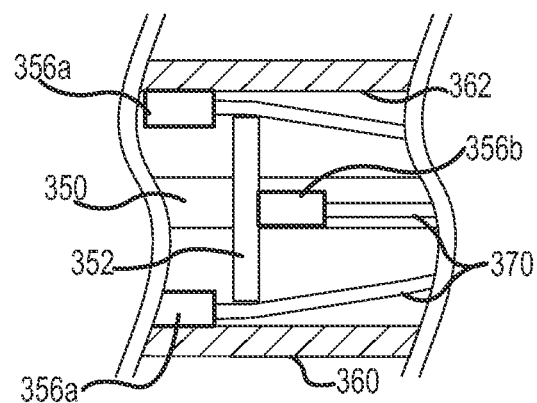
FIGS. 21A and 21B illustrate locking structures in other embodiments of the present invention.
Figure 21B:
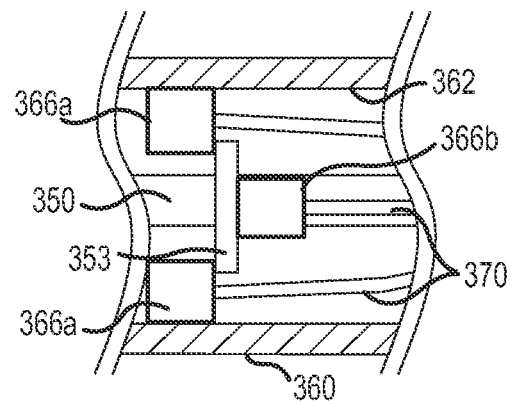

FIGS. 21A and 21B show in more detail alternative embodiments for locking a proximal end of a prosthesis to a guide that carries it. In the embodiment of FIG. 21A a radially extending member 352, in the form of a disk, is located on a segment of an elongate guide 350. Member 352 may also comprise rectangular, triangular, elliptical, or other geometric structures. Locking members 356a and 356b located at a proximal end of a prosthesis 370 are urged inward toward the elongate guide 350 by a force exerted on them by the inner wall 362 of sheath 360. The locking members 356a and 356b are attached directly to the struts of the main body of the prosthesis 370 or, alternatively, are attached to legs or other types of appendices that extend, or generally extend, proximally from the prosthesis. In the embodiment of FIG. 21A, radially extending member 352 has a relatively large outer dimension which facilitates the use of locking members 356a having relatively small outer dimensions. In the embodiment of FIG. 21B the radially extending member 353 has a smaller outer dimension than the radially extending member 352 shown in FIG. 21A. As a result, the locking members 366a associated with prosthesis 370 are made larger so that they properly engage with the inner wall 362 of sheath 360 and radially extending member 353. An advantage of this locking arrangement is that it facilitates the use of larger dimensioned locking members which is important if the locking members also function as radiopaque markers. Note also that in the embodiments of both FIGS. 21A and 21B at least portions of the prosthesis 370 are wedged between radially extending members 352 or 353 and the inner wall 362 of sheath 360. An advantage of this feature is that it can be used to further enhance the locking ability of the device.

FIGS. 18A and 18B depict a prosthesis delivery system 300 in another embodiment of the present invention. Delivery system 300 includes an elongate guide 312, having a proximal segment 314 and a smaller diameter distal segment 316. The distal segment 316 of guide 312 includes a proximal coil segment 318 and an end coil segment 321. The end coil segment 321 includes a distal tip section 322 and a proximal cap section 323. Positioned or formed on the distal segment 316 of guide 312 is a first radially extending member 319 having a proximal side 319a and a distal side 319b and a second radially extending member 320 having a proximal side 320a and a distal side 320b. Preferably, radially extending member 320 has an outer dimension smaller than the outer dimension of radially extending member 319. A radially self-expanding prosthesis, such as the prosthesis 130 earlier described in conjunction with FIG. 4C is positioned on the distal segment 316 of guide 312. When positioned on the guide 312, the longitudinal body portion of the prosthesis 130 resides between the first and second radially extending members 319 and 320 with locking members 136a residing on the proximal side 319a of member 319, locking members 136b residing on the distal side 319b of member 119, locking members 138a residing on the distal side 320b of member 320 and within the cap section 323 of distal coil segment 321 and locking members 138b residing on the proximal side 320a of member 320.

Figure 18C:
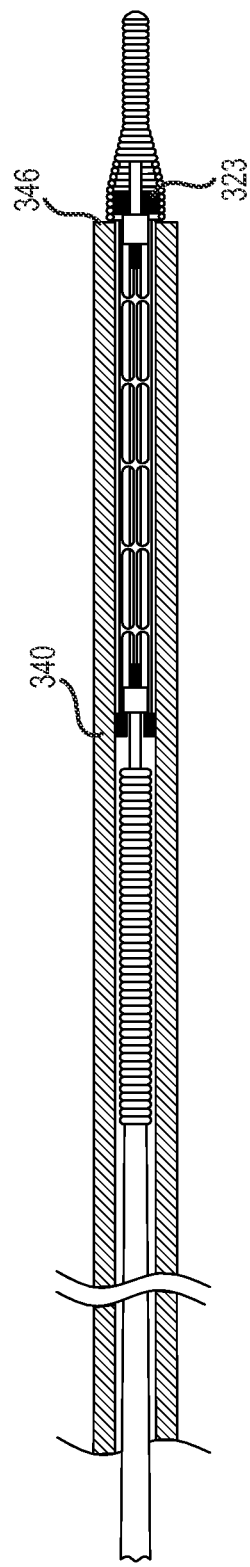

The prosthesis delivery system 300 includes a sheath 340 having an internal lumen 342 that contains the elongate guide 312 and prosthesis 130. The elongate guide 312 is positioned within sheath 340 such that a proximal end of the cap 323 is positioned within the distal end 346 of the sheath. In an alternative embodiment, as shown in FIG. 18C, cap 323 is positioned at the distal end 346 of the sheath 340, but not within it. In this manner, the distal tip section 322 assists in navigating the distal end of the catheter as it is advanced to the treatment site of a patient. In a preferred embodiment, distal tip section 322 comprises a radiopaque material which assists in visualizing the distal end of the delivery system during delivery and placement of the prosthesis. The distal end 346 of sheath 340 may also include a radiopaque marker 347. When the distal end 346 of sheath 340 is properly positioned at the treatment site, the sheath is withdrawn proximally to expose prosthesis 130. As the prosthesis expands locking members 138a move out of cap section 323 to enable the distal end 134 of the prosthesis 130 to fully expand. Further movement of the prosthesis out of sheath 340 continues to expand the prosthesis while the engagement of locking members 136 and radially extending member 319 continue to hold the proximal end 133 of the prosthesis securely to guide 312. Full expansion of prosthesis 130 is achieved when locking members 136a exit the distal end 346 of sheath 340. In an alternative embodiment, the position of cap section 323 with respect to radially extending member 320 and the dimensional characteristics of the cap 323, radially extending member 320 and locking members 138a and/or 138b are configured in a way that causes the distal end of the prosthesis 130 to remain locked onto the elongate guide until after the proximal end of the prosthesis has been released from the guide. In another embodiment, the distal locking structure is configured so that a twisting or forward advancement of the elongate guide 312 causes the locking members 138a and/or 138b to disengage with the radially extending member 320 and cap 323. In alternative embodiments, radially extending members 320 are omitted with the cap sections 323 alone restraining the locking members positioned at the distal end of the prosthesis.

The prosthesis delivery system 350 of FIGS. 19A and 19B is similar to the delivery system 300 of FIGS. 18A and 18B with two exceptions. The first exception is that the proximal cap section 323 of distal coil segment 321 is longer and is positioned to entirely cover radially extending member 320. The second exception is that the distal end 134 of prosthesis 130 includes only locking members 138b and not locking members 138a.

In the embodiment of FIGS. 20A and 20B a system 400 is provided for delivering multiple prostheses 430a and 430b in tandem. The manner in which each of prostheses 430a and 430b are secured to elongate guide 412 is similar to how prosthesis 130 is secured to elongate guide 112 in the embodiments of FIGS. 4A, 4B and 4C. In the embodiment of FIGS. 20A and 20B elongate guide 412 has four radially extending members 419a, 420a, 419b and 420b located on its distal segment 416. The proximal and distal ends of prosthesis 430a are locked on the guide 412 by the cooperative engagement of locking member 436a and radially extending members 419a and 420a. Likewise, the proximal and distal ends of prosthesis 430b are locked on the guide 412 by the cooperative engagement of locking member 436b and radially extending members 419b and 420b. In an alternative embodiment, only radially extending members 419a and 419b are provided on the guide 412. In such an embodiment, only the proximal ends of prostheses 430a and 430b are locked on the guide.

As previously discussed, the radially extending members that constitute an integral part of the locking structures of the present invention can take many forms. A sample of these forms is shown in the embodiments of FIGS. 22 through 26. The locking arrangement of FIGS. 22A and 22B includes a radially extending member 500 located on a distal segment of an elongate guide 450. Locking members 456a and 456b located at a proximal end of a prosthesis 470 are urged inward toward the elongate guide 450 by a force exerted on them by the inner wall 462 of a sheath 460. The locking members 456a and 456b are attached directly to the struts of the main body of the prosthesis 470 or, alternatively, are attached to legs or other types of appendices that extend, or generally extend, proximally from the prosthesis. In the embodiment of FIGS. 22A and 22B, the end portions of the prosthesis 470, whether they be the struts that form the main body of the prosthesis or extensions therefrom, reside within recesses 482 formed along the outer circumference of radially extending member 500. Placement of the end portions of the prosthesis within recesses 482 provides a number of advantages. First, the profile of the locking structure is reduced. Second, as can be seen by a comparative look of FIG. 21 and FIG. 22, the contact surface area between locking members 456a and radially extending member 500 is maximized or made greater by the inclusion of recesses 482. This results in a more reliable locking structure. Third, no part of radially extending member 500 imposes a force on the prosthesis itself. This minimizes the likelihood of prosthesis fractures and can enhance the shelf-life of the delivery system. Radially extending member 500 also includes a central opening 480 that has a diameter slightly larger than the distal segment of the elongate guide. In this manner, member 500 can be slid onto the distal segment of elongate guide 450 and affixed thereto by soldering, welding or by the use of an adhesive. In one embodiment the recesses 482 are dimensioned to be only slightly larger than the prosthesis portions residing in them to create a close fitting locking structure. The close fitting structure minimizes movement of the prosthesis during delivery which is important when the outer and/or inner surfaces of the prosthesis possess a coating, such as a drug coating. The close fitting structure also enables a more precise deployment of the prosthesis. In another embodiment, radially extending member 500 and locking members 456a and 456b are sized so that their outer circumferential surfaces are flush or substantially flush with one another.

In the embodiment of FIG. 23 a radially extending member 510 is provided having a proximal flat surface 512 and a concave distal surface 514. As shown, locking members 456a are positioned to abut flat surface 512 while locking members 456b are positioned to abut concave surface 514. In an alternative embodiment, the proximal surface is made concave while distal surface is made flat. In yet another embodiment, both the proximal and distal surfaces are made concave. The use of the concave surface 514 permits the locking members 456a and 456b of the prosthesis to be more closely spaced to one another.

In the embodiment of FIG. 24, a radially extending member 516 is provided that has a flat distal surface 517 and a front face comprising an annular recess 518. Locking members 456a of prosthesis 470 have small distal extensions 457 that are configured to reside within the annular recess 518 when the prosthesis is positioned on the guide 450 in a delivery position.

Figure 25A:
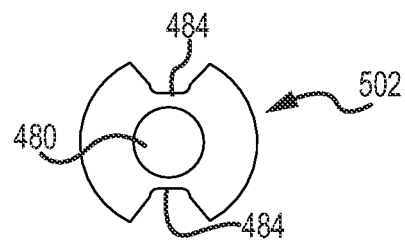
FIGS. 25A-D illustrate radially extending members in alternative embodiments of the present invention.
Figure 25B:
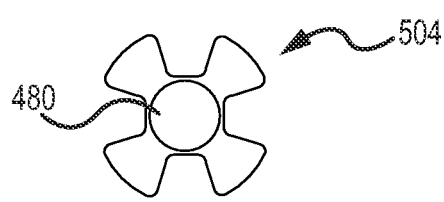
Figure 25C:
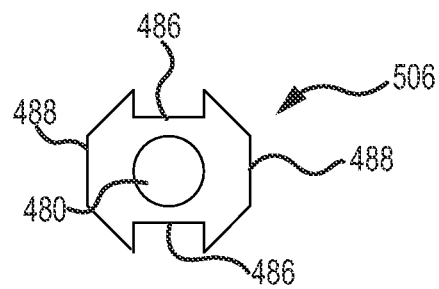
Figure 25D:
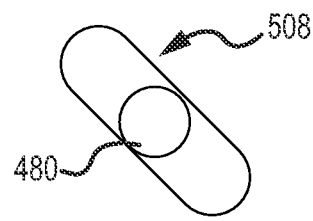

FIGS. 25A-D illustrate radially extending members in other embodiments. In each of the designs, a central opening 480 is provided to facilitate placement and attachment of the members to a distal segment of an elongate guide. In FIG. 25A, radially extending member 502 includes two recesses 484 that are wider than the recesses 482 provided in the embodiment of FIGS. 22A and 22B. The wider recesses 484 make loading of the prosthesis onto the elongate guide easier. In embodiments where locking members 456a are attached to the end peak segments of a prosthesis, the width of recesses 484 are made wide enough to accommodate the peak segments. In an alternative embodiment where the proximal end of a prosthesis is equipped with only one of locking member 456a, (see also FIG. 2 where only one of locking member 36a is provided) a radially extending member having a single recess is provided. Moreover, as shown in FIG. 25B, in some embodiments a radially extending member 504 having greater than two recesses is provided. FIG. 25C depicts a radially extending member 506 in another embodiment. Member 506 includes two recesses 486 and two flat surfaces 488 located at 90 degrees to the recesses. FIG. 25D illustrates a radially extending member 508 in yet another embodiment.

Figure 27:
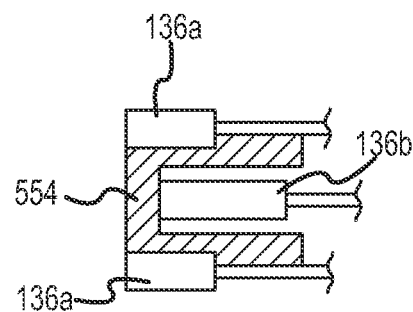
FIG. 27 illustrates a radially extending member in another embodiment of the present invention.

FIGS. 26A-C illustrates a prosthesis delivery system 550 in another embodiment of the invention. The delivery system includes an elongate guide 552 with a similar construction to the elongate guides previously herein described. The prosthesis carried by elongate guide 552 has a construction similar to prosthesis 130 depicted in FIG. 4C. As such like references are used to describe the prosthesis. As shown, prosthesis 130 is in an unexpanded state and mounted on the distal segment of guide 552. Located on guide 552 is a radially extending member 554 that is configured to engage with the locking members 136a and 136b positioned at the proximal end 133 of prosthesis 130. Radially extending member 554 comprises a cylindrical proximal portion 555 having a central lumen 556 that has a diameter slightly larger than the distal segment 553 of guide 552. Central lumen 556 is provided to facilitate placement and attachment of the radially extending member 554 to the distal segment 553 of elongate guide 552. Extending distally from cylindrical portion 555 are arms 557 and 558 that form a recess 559. As shown in FIG. 26A, locking members 136a sit on an outer surface 560 of cylindrical portion 555 with locking members 136b positioned within recess 559. In a preferred embodiment, the inner surfaces of recess 559 overlap with the outer surface 560 of cylindrical portion 555 by some distance "d" as shown in FIG. 26C. This results in a reduced spacing between the proximal ends of locking members 136a and 136b. In another embodiment, the depth of recess 559 extends further into the proximal cylindrical portion 555 creating a larger overlap between locking members 136a and 136b as shown in FIG. 27. An advantage of overlapping locking members 136a and 136b is that it permits prosthesis 130 to be manufactured more similar to conventional prostheses by minimizing the extent by which the proximal prosthesis elements are staggered one from another. When locking members 136a and 136b also function as radiopaque markers, overlapping of the members enhances their visual effect under fluoroscopy. For this reason, the use of smaller dimensioned locking members is facilitated.

Figure 28:
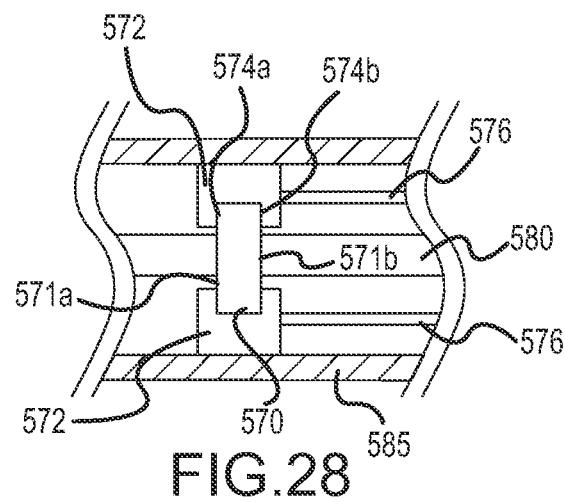
FIG. 28 illustrates a locking structure in an embodiment of the present invention.

FIG. 28 illustrates a locking arrangement between a prosthesis and an elongate guide in another embodiment of the present invention. The embodiment includes a radially extending member 570 positioned on a guide 580. Radially extending member 570 has a proximal side 571a and a distal side 571b. Associated with the prosthesis are generally U-shaped locking members 572 that are attached to the prosthesis by proximally extending legs 576. In practice, a sheath, catheter or like device 585 exerts an inward force on the locking members 572 so that it cradles at least a portion of the radially extending member 570, as shown in FIG. 28, so that the opposing surfaces 574a and 574b of locking members 572 are positioned to act upon the proximal and distal side surfaces 571a and 571b, respectively. An advantage of the embodiment of FIG. 28, as well as the embodiment of FIG. 29 described below, is that it does not require a staggered arrangement of locking members to function. In addition, although a plurality of locking members 570 are illustrated in FIG. 28, it is appreciated a single locking member 570 may be used to effectuate a locking of the prosthesis onto the elongate guide.

Figure 29:
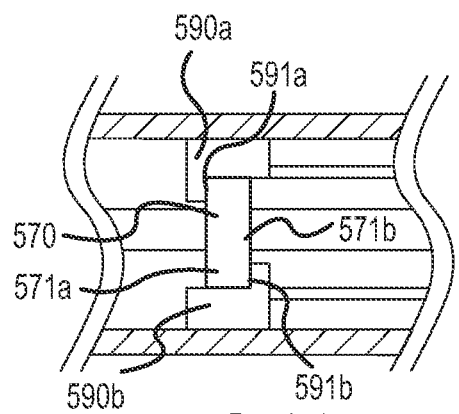
FIG. 29 illustrates a locking structure in another embodiment of the present invention.

FIG. 29 illustrates a locking arrangement in another embodiment of the invention that is similar to that shown in FIG. 28. In the embodiment of FIG. 29 locking members 590a and 590b are generally L-shaped instead of being U-shaped. Locking member 590a has at a proximal end a surface 591a that is configured to abut the proximal side surface 571a of radially extending member 570. Locking member 590b, on the other hand, has at a distal end a surface 591b that is configured to abut the distal side 571b of radially extending member 570.

Figure 30:
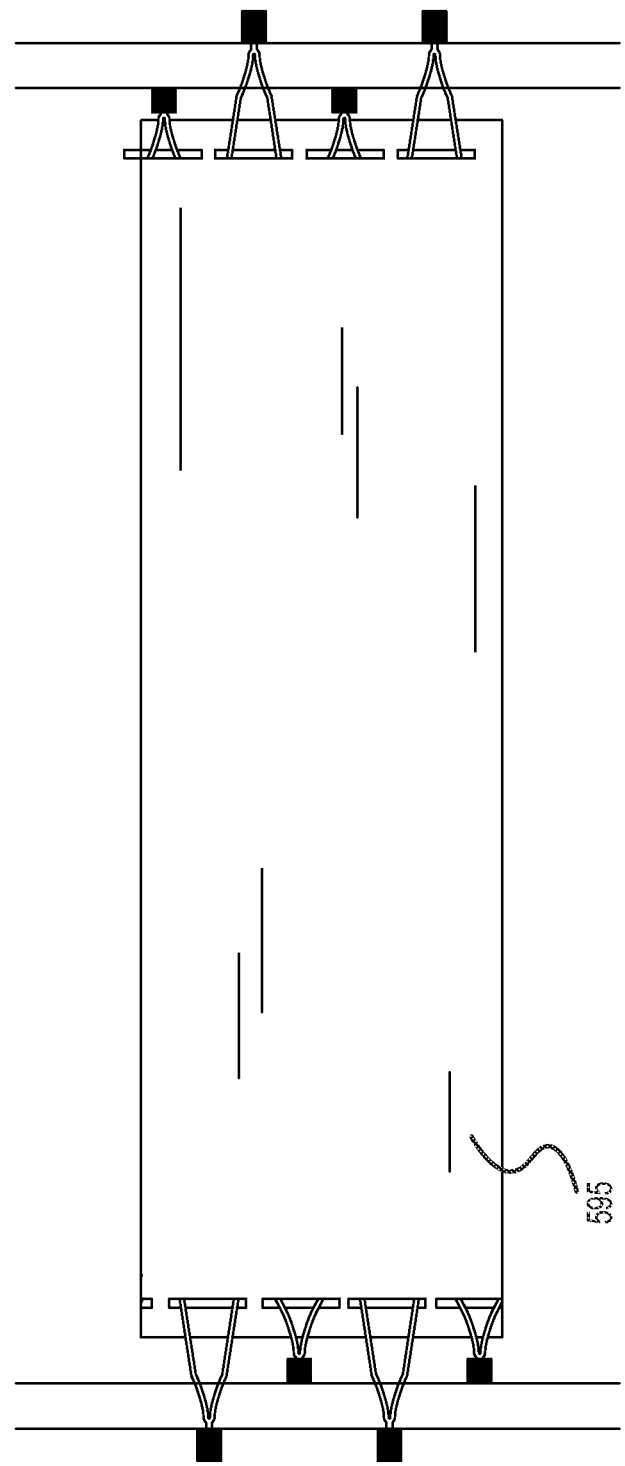
FIG. 30 illustrates a covered prosthesis in an embodiment of the present invention.
Figure 31A:
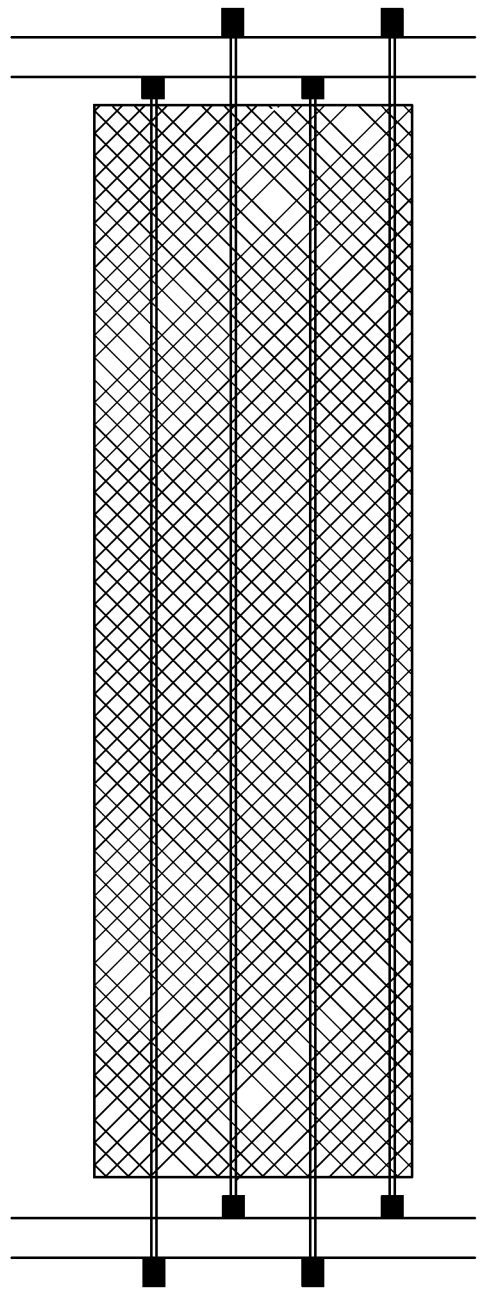
FIGS. 31A and 31B illustrate braided prostheses in alternative embodiments of the present invention.
Figure 31B:
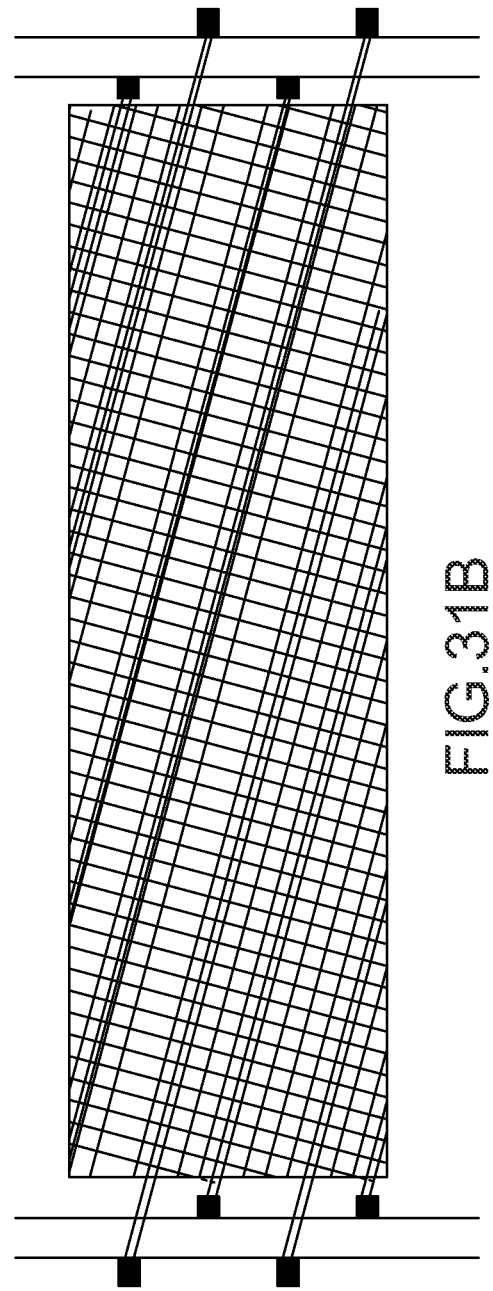
Figure 32:
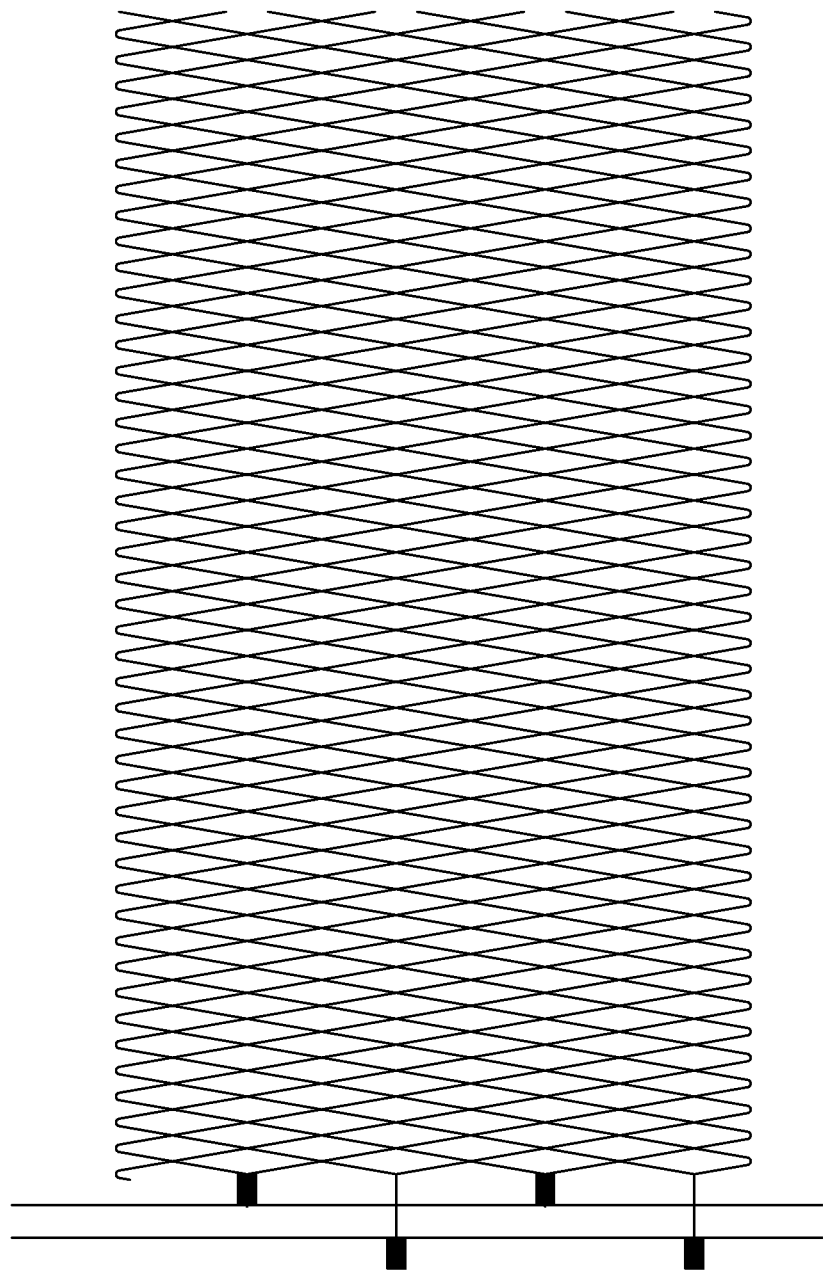
FIG. 32 illustrates a flow diverter in an embodiment of the present invention.

FIGS. 30-32 show different types of prosthesis and delivery systems that may incorporate the locking features of the present invention. FIG. 30 is a prosthesis having biocompatible covering 595. FIGS. 31A and 31B show different variations of a braided prosthesis. FIG. 32 is a braided flow diverter.

With reference to FIGS. 33-36, alternative prosthesis and prosthesis delivery system are illustrated. In FIG. 33, a prosthesis 600 having a proximal end 601 and a distal end 603 is shown with its proximal end 601 locked onto a radially extending member 619. Radially extending member 619 extends radially from a guide (not shown) and has a proximal side 619a and a distal side 619b. A locking feature 604 comprising a leg 605 that contains a first locking member 606a and a second locking member 606b is attached to the proximal end 601 of prosthesis 600. The locking members are spaced on the leg 605 so that locking member 606a is in an abutting, or near abutting, relationship with the proximal side 619a of member 619 and so that locking member 606b is in an abutting, or near abutting, relationship with the distal side 619b of member 619. In practice, a sheath, catheter or like device is positioned over the apparatus and provides a compression force that urges the locking members 619a and 619b into position about the radially extending member 619.

Figure 37A:
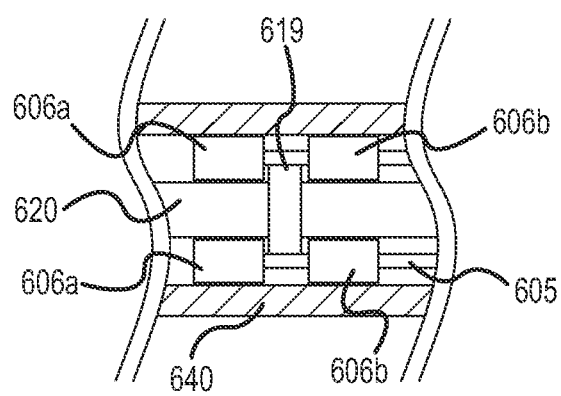
FIGS. 37A and 37B illustrates locking structures in alternative embodiments of the present invention.
Figure 37B:
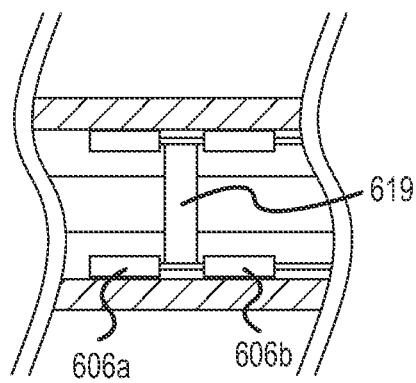

In the embodiment of FIG. 34, the proximal end 601 of prosthesis 600 has a plurality of locking features 604. In addition, the distal end 603 of prosthesis includes one or a plurality of radiopaque markers 610. FIG. 37A shows an enlarged view of the locking arrangement of FIG. 34. As shown, radially extending member 619 is positioned on an elongate guide 620 that carries the prosthesis 600 (not shown). Each of locking members 606a and 606b is positioned on opposite sides of the radially extending member 619 to, in effect, sandwich member 619 between the two locking members. A sheath, catheter or like device 640 contains the apparatus and provides the compression forces to hold the locking members onto the radially extending member 619. In the embodiment of FIG. 37B, radially extending member 619 has a larger outer dimension that enables the use of smaller dimensioned locking members 606a and 606b.

Figure 35:
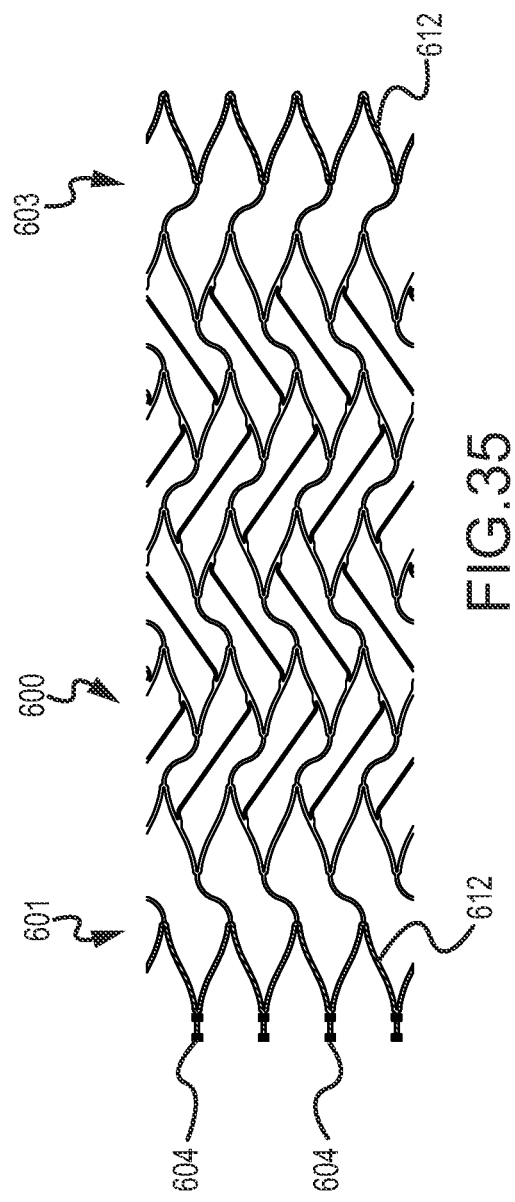
FIG. 35 illustrates a locking arrangement in another embodiment of the present invention.
Figure 36:
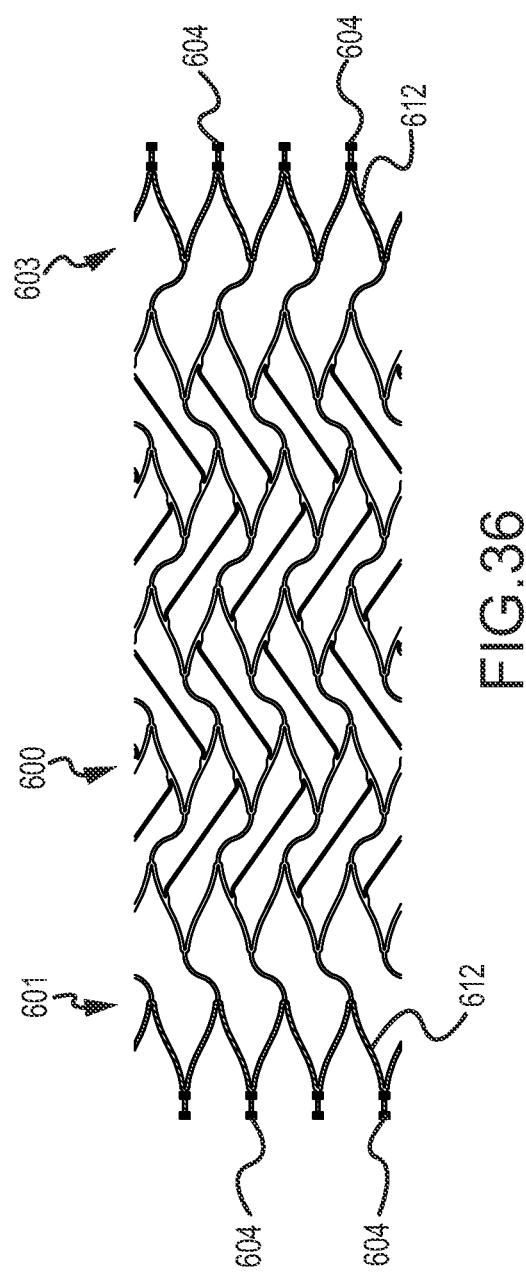
FIG. 36 illustrates a locking arrangement in yet another embodiment of the present invention.

In the embodiment of FIG. 35, the proximal end 601 and distal end 603 of prosthesis 600 are coated with a radiopaque material 612 to enhance visualization of the prosthesis ends under fluoroscopy. Prosthesis 600 also has at its proximal end 601 a plurality of locking features 604. In the embodiment of FIG. 36, prosthesis 600 also has at its distal end 603 a plurality of locking features 604.

FIGS. 38A and 38B illustrate a prosthesis 700 in another embodiment of the invention. Prosthesis 700 includes a proximal end 701 and a distal end 702. Extending from each end of the prosthesis are legs 705 that include inwardly projecting elements 706. When the prosthesis 700 is positioned on an elongate guide (not shown) the legs 705 are urged inward by a sheath or catheter (not shown) to engage a radially extending member 719 positioned on the guide. When in a locking position, as shown in FIG. 38B, the inner faces 707 of elements 706 are positioned to engage the outside surface 719a of radially extending members 719.

In the embodiment of FIG. 38C, legs 705 include at their tip a radiopaque marker 712 that has an inner surface 713 that engages the outside surface of radially extending member 719. The legs 705 also include inwardly projecting elements 710 that are spaced from the radiopaque markers 712 by a distance equal to or slightly larger than the width of the radially extending member 719. The projecting elements 710 have inner faces 711 that are configured to engage with the inside surface 719b of member 719. FIGS. 38D and 38E show additional embodiments wherein the legs 705 include features 750 that cradle and lock the ends of the prosthesis in position in a manner similar to that described in the embodiment of FIG. 28.

Figure 39A:
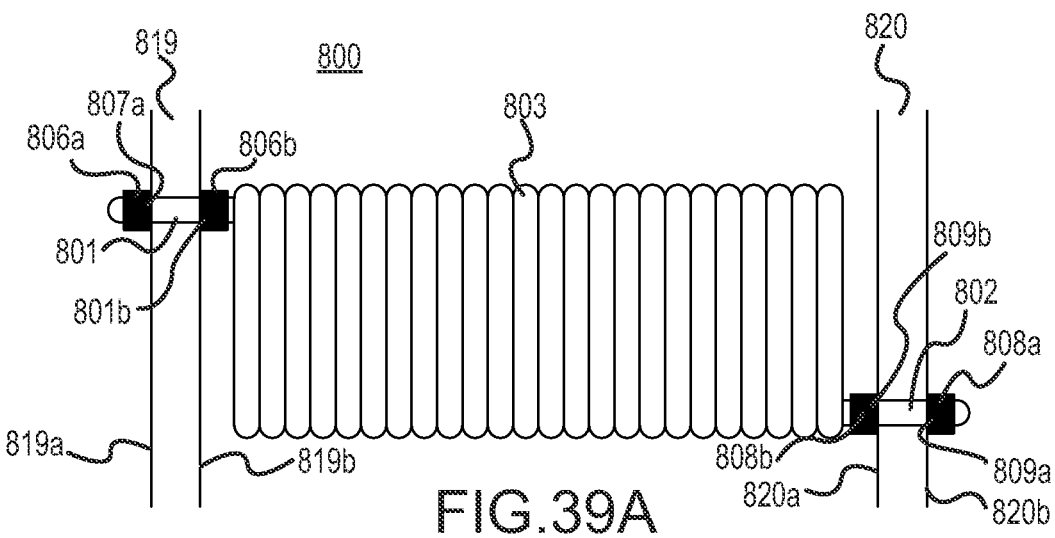
FIGS. 39A-C illustrate coil stents in alternative embodiments of the present invention.
Figure 39B:
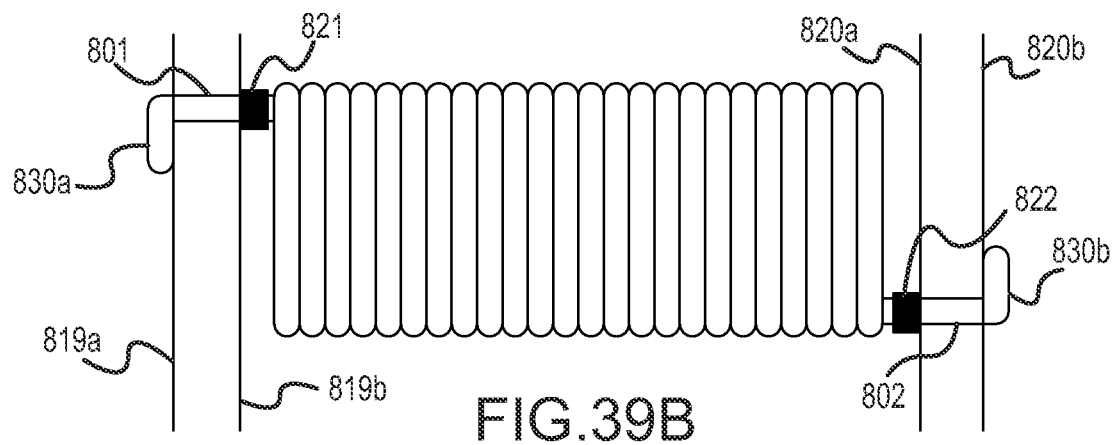
Figure 39C:
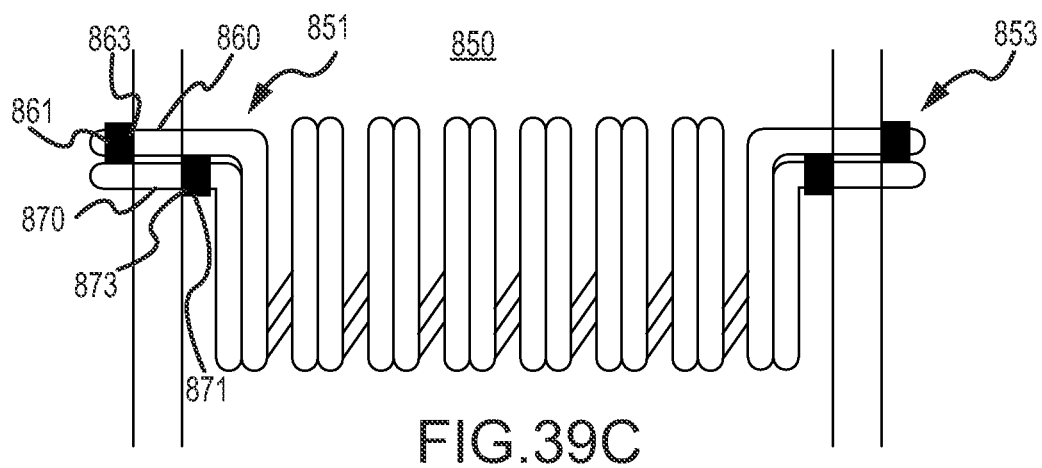

FIGS. 39A-C illustrate various methods for locking the ends of a coil stent to an elongate guide. In FIG. 39A, stent 800 is made of a single, helically wound wire having a proximal end 801 and a distal end 802. When positioned on a delivery guide (not shown), the longitudinal body portion 803 of the stent is positioned between a first radially extending member 819 and a second radially extending member 820. Member 819 has a proximal surface 819a and a distal surface 819b. Likewise, member 820 has a proximal surface 820a and a distal surface 820b. The proximal end 801 of the wire has attached to it two spaced-apart locking members 806a and 806b that are positioned on opposite sides of radially extending member 819 so that a distal end surface 807a of locking member 806a abuts surface 819a of member 819 and so that a proximal end surface 807b of locking member 806b abuts surface 819b of member 819. The distal end 802 of the wire also has attached to it two spaced-apart locking members 808a and 808b that are positioned on opposite sides of radially extending member 820 so that a distal end surface 809b of locking member 808b abuts surface 820a of member 820 and so that a proximal end surface 809a of locking member 808a abuts surface 820b of member 820. The locking method of FIG. 39A is similar to the locking method previously described in conjunction with the embodiments of FIGS. 33-37.

In the embodiment of FIG. 39B, the proximal end segment 801 of the stent wire is bent to form a hook 830a. The proximal end segment also includes a locking member 821 that is spaced a distance from the hook 830a, the distance being approximately the width of radially extending member 819. The distal end segment 802 of the stent wire is also bent to form a hook 830b and includes a locking member 822 that is spaced from the hook 830b by a distance approximately equal to the width of radially extending member 820. Locking of the stent ends to the elongate guide (not shown) is accomplished by sandwiching the radially extending members between the hook and locking members located at each end segment of the stent.

The stent 850 of FIG. 39C comprises a double helically wound stent that has two wire end segments located at each end of the stent. The two wire segments 860 and 870 at the proximal end 851 of stent 850 each have attached thereto a locking member. Attached to wire segment 860 is locking member 861. Attached to wire segment 870 is locking member 871. Locking member 861 and 871 are positioned on their respective wire segments such that locking member 861 is positioned proximal to locking member 871. The spacing between the locking members 861 and 871 is equal to or slightly larger than the width of radially extending member 819. In use, locking members 861 and 871 are urged inward by a compression force applied by a sheath so that a distal end surface 863 of locking member 861 abuts, or nearly abuts, the proximal side 819a of radially extending member 819 and so that a proximal end 873 of locking member 871 abuts, or nearly abuts, the distal side 819b of radially extending member 19. Locking of the distal end 853 of stent 850 is accomplished in a like manner.

Figure 40:
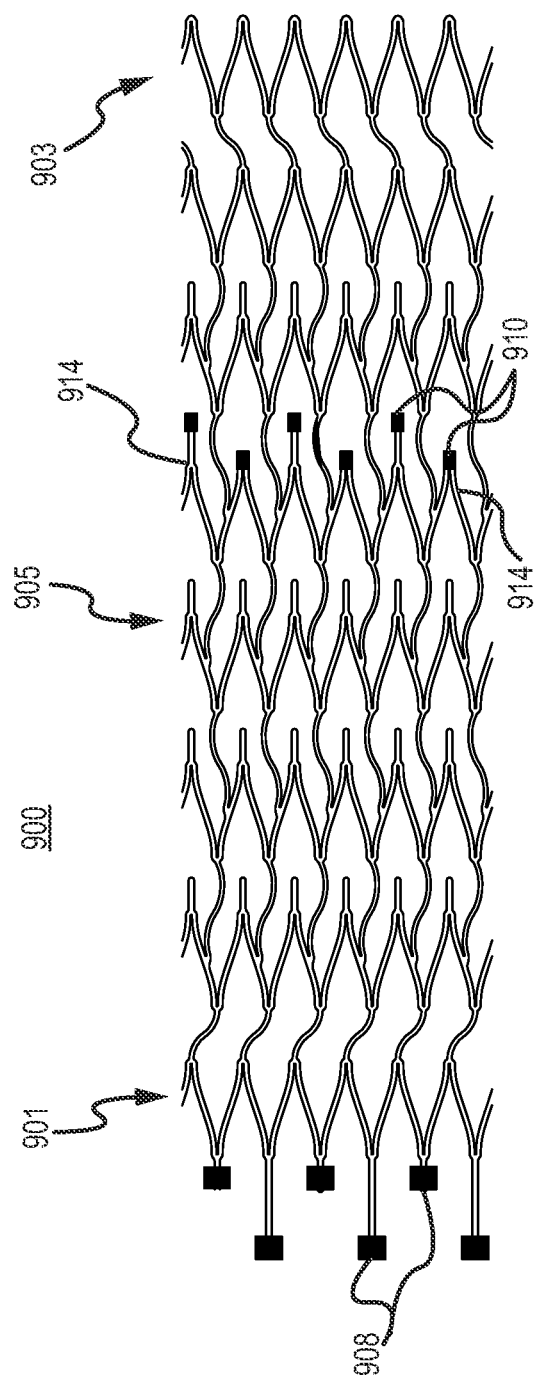
FIG. 40 illustrates a prosthesis in another embodiment of the present invention.

Until now, all of the embodiments described herein have involved locking an end of a prosthesis to an elongate guide that carries it. It is appreciated, however, that the present invention is not limited to locking only the ends of a prosthesis to a delivery guide. In accordance with another aspect of the present invention a prosthesis 900 is provided, as shown in FIG. 40, having a proximal end 901, a distal end 903, and a longitudinal body portion 905 disposed between the proximal and distal ends. Similar to other embodiments described herein, the proximal end 901 of the prosthesis includes a plurality of locking members 908 that are configured to cooperate with one or more features on an elongate guide to lock the end to the guide. Prosthesis 900 also has a set of locking members 910 located within the longitudinal body portion 905 of the prosthesis which are configured to cooperate with features on an elongate guide to lock an internal segment of the prosthesis to the guide. In the embodiment of FIG. 40, the body portion 905 of the prosthesis comprises a plurality of unconnected peak segments 914 that are used for mounting the locking members 910 onto the prosthesis. In an alternative embodiment, locking members like those shown in FIG. 14 are attached to struts, other than peak segments, located within the body portion 905 of prosthesis 900.

As previously discussed, the prosthesis delivery systems of the present invention may be delivered to a treatment site within a patient by a variety of means. One method is to position a distal end of a delivery catheter across the treatment site and subsequently advancing the prosthesis delivery system through a lumen of the catheter until the prosthesis reaches the end of the catheter. The prosthesis is then deployed by holding the elongate guide in place and slowly retracting the catheter. Radiopaque markers strategically positioned on the prosthesis, elongate guide and catheter are used to mark the placement of the various components during the treatment procedure. To limit blood loss from a patient during a vascular procedure, a rotary hemostatic valve (RHV) is typically attached to a luer at the proximal end of the catheter with the delivery system being delivered through the RHV.

Figure 41:
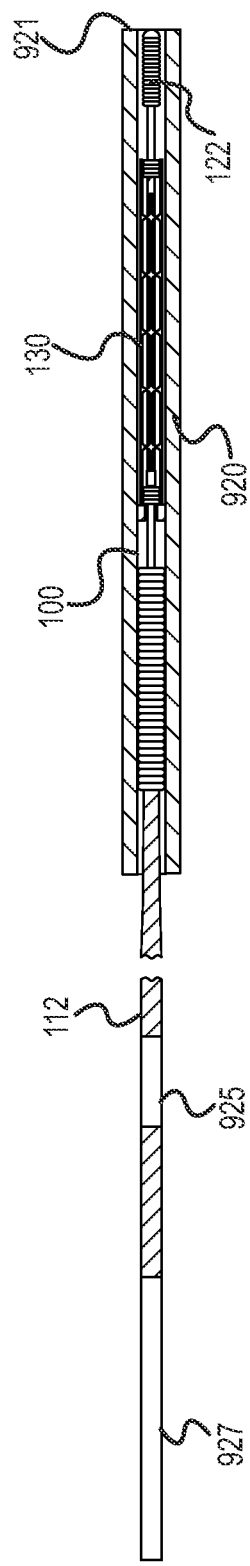
FIG. 41 illustrates the prosthesis delivery system of FIG. 4 in a packaging sheath in one embodiment of the present invention.
Figure 42:
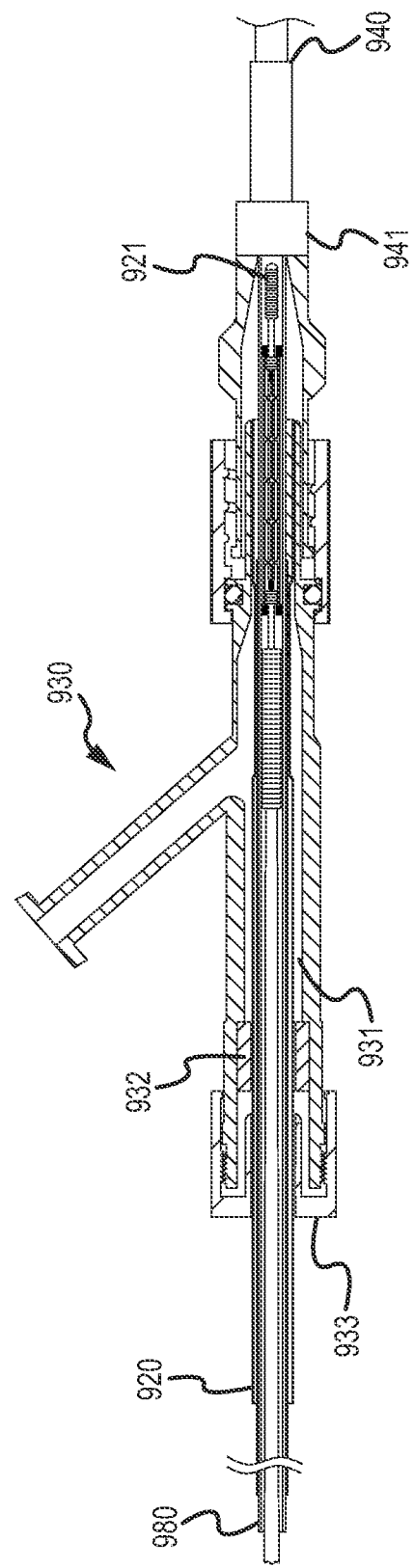
FIG. 42 shows the apparatus of FIG. 41 situated within the body of a hemostatic valve.

FIG. 41 shows the prosthesis delivery system 100 of FIGS. 4A-C having a about its distal end a packaging sheath 920. The packaging sheath 920 is used to constrain the prosthesis 130 onto the elongate guide 112 after the prosthesis is mounted on the guide with the distal end 122 of the guide being generally aligned with the distal end 921 of the sheath 920. Pursuant to one method as shown in FIG. 42 placement of the delivery system is achieved by first inserting the sheathed distal end of the delivery system into the body 931 of a RHV 930 that is connected to the proximal end 941 of a delivery catheter 940. The distal end of the delivery system 100 is inserted into the RHV until the distal end 921 abuts the proximal end 941 (typically a luer) of catheter 940. Once in this position a locking gasket 932 in the RHV body is made to press against the packaging sheath to impede blood flow and to also lock the packaging sheath in position with respect to the RHV. In one embodiment, as shown in FIG. 41, two sets of markings 925 and 927 are provided on the proximal segment 114 of guide 112. Pursuant to one delivery method, the elongate guide is advanced to push the prosthesis through the delivery catheter 940 until marking 927 approaches the proximal end 980 of packaging sheath 920. At this point, the RHV is loosened and the packaging sheath 920 is slid off the proximal end of the guide 112. Maintaining the packaging sheath 920 within the RHV 930 during the procedure provides extra guide support that inhibits kinking of the elongate guide 112 when the delivery system is initially being advanced through the catheter 940. Upon retightening of the RHV, the guide is advanced until marking 925 approaches the proximal end 933 of the RHV 930. At this point the prosthesis 130 is known to be nearing the distal end of the delivery catheter 940. In practice, the physician can use marking 925 as a reference to begin viewing the treatment site under fluoroscopy. An advantage of marking 925 is that, during delivery of the prosthesis, it can postpone the need to view the treatment site under fluoroscopy until the prosthesis is known to be near the treatment site. This reduces exposure time to both the patient and the attending surgical staff. In an exemplary embodiment, elongate guide 112 has a length of about 200 centimeters with marking 925 and 927 being spaced proximally from the distal end of the elongate guide by about 165 centimeters and about 190 centimeters, respectively. In other embodiments, when a portion of the packaging sheath 920 extends some distance outside the proximal end 933 of the RHV 930, as shown in FIG. 42, the marking 925 may be placed proximal to marking 927.

Figure 43:
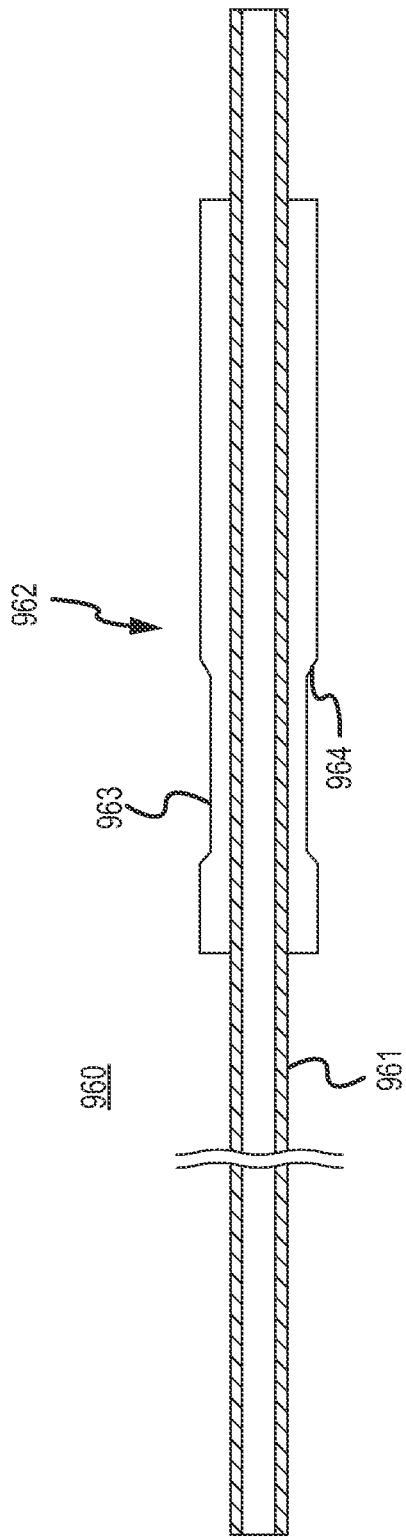
FIG. 43 illustrates a packaging sheath in another embodiment of the present invention.
Figure 44:
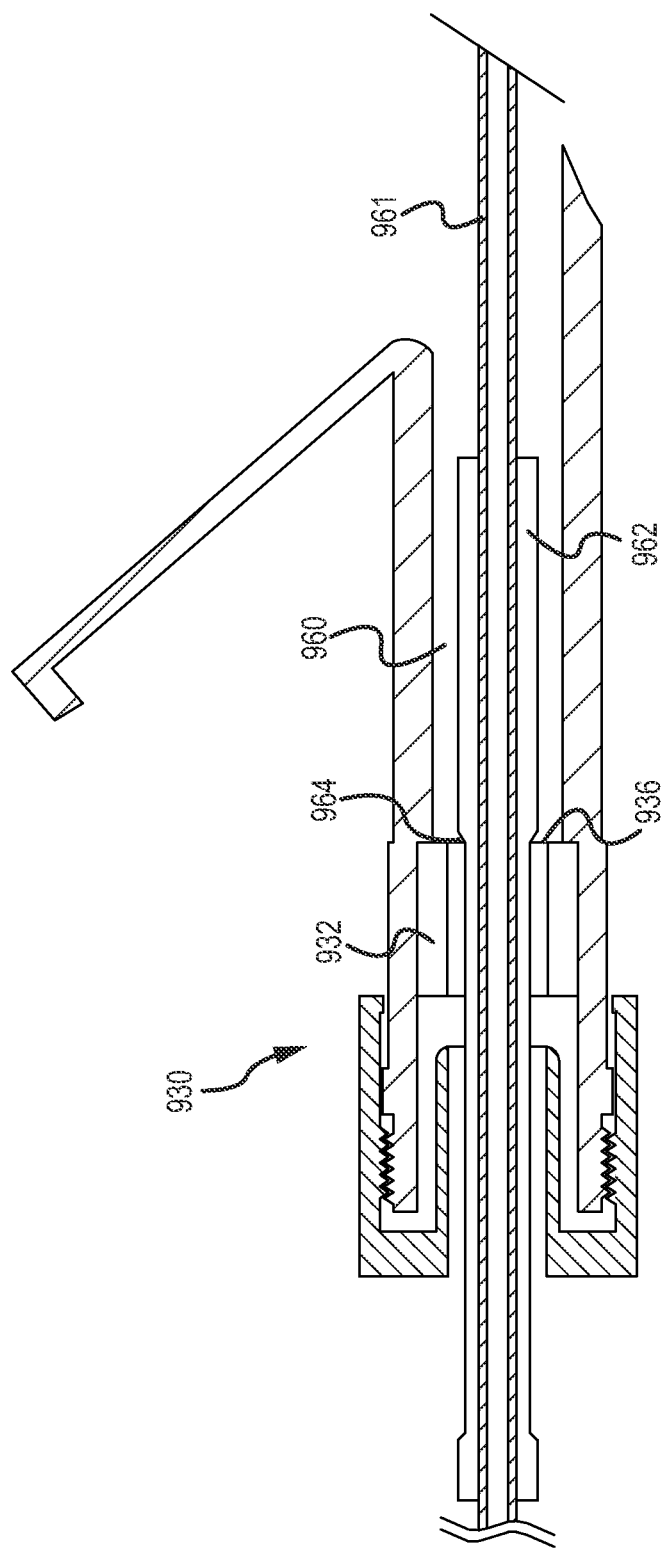
FIG. 44 illustrates shows the packaging sheath of FIG. 43 situated within the body portion of a hemostatic valve.

Because the outer dimensions of wire based prosthesis delivery systems are typically very small, they tend not to fit well within conventional RHVs. To solve this problem, the embodiment of FIG. 43 provides a packaging sheath 960 that includes an inner polymeric tube 961 that is dimensioned to receive the distal end of a prosthesis delivery system. Attached to or integrally formed with inner tube 961 is a larger diameter segment 962 that may or may not include a recessed section 963. Preferably segment 962 is made of a polymer that is more compliant than that of the inner tube 961. In one embodiment inner tube 961 has an inner and outer diameter of about 0.019 inches and 0.030 inches, respectively, with the largest outer dimension/diameter of segment 962 being about 0.050 inches. In one embodiment, as shown in FIG. 44, the packaging sheath 960 is positioned within the RHV 930 so that a ridge 964 created by recess section 963 abuts the distal edge 936 of locking gasket 932. Abutment between packaging sheath 962 and locking gasket 932 assists in inhibiting proximal movement of the sheath within the RHV body.

While the above description contains many specifics, those specifics should not be construed as limitations on the scope of the disclosure, but merely as exemplifications of preferred embodiments thereof. For example, dimensions other than those listed above are contemplated. In addition, it is important to note that each of the locking structures and/or arrangements described herein may be used to lock or inhibit movement of either of the proximal end or distal end (or both) of a prosthesis positioned on an elongate guide although they have been disclosed as residing at one end or the other. Moreover, for the sake of clarity, not every conceivable combination of locking structures has been disclosed. However, it is appreciated that many of the features disclosed herein are interchangeable among the various embodiments. Those skilled in the art will envision many other possible variations that are within the scope and spirit of the disclosure. Further, it is to be appreciated that the delivery of a prosthesis pursuant to any of the embodiments disclosed herein is achievable with the use of a sheath or a catheter or any other device that is capable of constraining and locking one or both ends of the prosthesis to a guide that carries it.

What is claimed is:

1. A prosthesis delivery system comprising:

a prosthesis having a longitudinal body generally disposed about an axis, the longitudinal body having proximal and distal ends, the proximal end of the prosthesis having a proximal locking device comprising a first proximal extension extending proximally from the proximal end of the longitudinal body, the first proximal extension having located thereon first and second radially extending and spaced-apart locking members, the first locking member having a first proximal facing surface and the second locking member having a first distal facing surface, the first proximal facing surface and the first distal facing surface opposing one another, the first proximal facing surface and the first distal facing surface being spaced-apart by the first distance;

an elongate flexible guide having a proximal section and a distal section, the distal section configured for mounting the prosthesis and having a first radially extending member positioned proximal to a distal end of the elongate guide and having a width approximately equal to the first distance, the first radially extending member having a second proximal facing surface and a second distal facing surface, the prosthesis being mounted on the distal section of the elongate guide, the first proximal facing surface positioned to abut or nearly abut the second distal facing surface and the first distal facing surface positioned to abut or nearly abut the second proximal facing surface, wherein the first radially extending member comprises a cylindrical member that is sandwiched between the first and second locking members, the cylindrical member comprising a coil; and a sheath disposed over at least a portion of the elongate guide to constrain the prosthesis on the elongate guide.

2. A prosthesis delivery system comprising:

a prosthesis having a longitudinal body generally disposed about an axis, the longitudinal body having proximal and distal ends, the proximal end of the prosthesis having a proximal locking device comprising a first proximal extension extending proximally from the proximal end of the longitudinal body, the first proximal extension having located thereon first and second radially extending and spaced-apart locking members, the first locking member having a first proximal facing surface and the second locking member having a first distal facing surface, the first proximal facing surface and the first distal facing surface opposing one another, the first proximal facing surface and the first distal facing surface being spaced-apart by the first distance;

an elongate flexible guide having a proximal section and a distal section, the distal section configured for mounting the prosthesis and having a first radially extending member positioned proximal to a distal end of the elongate guide and having a width approximately equal to the first distance, the first radially extending member having a second proximal facing surface and a second distal facing surface, the prosthesis being mounted on the distal section of the elongate guide, the first proximal facing surface positioned to abut or nearly abut the second distal facing surface and the first distal facing surface positioned to abut or nearly abut the second proximal facing surface;

a second radially extending member positioned distal to the first radially extending member and proximal to the distal end of the elongate guide, the second radially extending member having a third proximal facing surface and a third distal facing surface, the prosthesis having at least one feature in abutting or near abutting relationship to the third proximal facing surface and/or the third distal facing surface of the second radially extending member; and a sheath disposed over at least a portion of the elongate guide to constrain the prosthesis on the elongate guide.

3. The prosthesis delivery system according to claim 2 wherein the at least one feature comprises a radiopaque material.

4. The prosthesis delivery system according to claim 2 wherein the second radially extending member comprises a radiopaque material.

* * * * *